(12) United States Patent
Mirmira et al.

(10) Patent No.: US 10,738,343 B2
(45) Date of Patent: Aug. 11, 2020

(54) EXTRACELLULAR VESICLE RIBONUCLEIC ACID (RNA) CARGO AS A BIOMARKER OF HYPERGLYCEMIA AND TYPE 1 DIABETES

(71) Applicants: The Trustees of Indiana University, Indianapolis, IN (US); The United States Government as represented by the Department of Veterans Affairs, Washington, DC (US)

(72) Inventors: Raghavendra G. Mirmira, Zionsville, IN (US); Carmella Evans-Molina, Zionsville, IN (US); Emily K. Sims, Carmel, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 0 days.

(21) Appl. No.: 16/250,466

(22) Filed: Jan. 17, 2019

(65) Prior Publication Data

US 2019/0226006 A1    Jul. 25, 2019

Related U.S. Application Data

(60) Provisional application No. 62/619,464, filed on Jan. 19, 2018.

(51) Int. Cl.

| | |
|---|---|
| *A61K 48/00* | (2006.01) |
| *C07H 21/04* | (2006.01) |
| *C12Q 1/06* | (2006.01) |
| *C12Q 1/686* | (2018.01) |
| *C12Q 1/54* | (2006.01) |
| *G01N 33/49* | (2006.01) |
| *C12Q 1/6883* | (2018.01) |

(52) U.S. Cl.
CPC ................ *C12Q 1/06* (2013.01); *C12Q 1/54* (2013.01); *C12Q 1/686* (2013.01); *C12Q 1/6883* (2013.01); *G01N 33/49* (2013.01); *C12Q 2600/112* (2013.01); *C12Q 2600/178* (2013.01); *G01N 2800/042* (2013.01)

(58) Field of Classification Search
CPC ........................... A61K 31/713; C12N 15/115
See application file for complete search history.

(56) References Cited

U.S. PATENT DOCUMENTS

| | | | |
|---|---|---|---|
| 2016/0378937 A1* | 12/2016 | Soni .................. | G06N 5/047 705/3 |
| 2019/0183919 A1* | 6/2019 | Krolewski .............. | A61K 45/06 |

FOREIGN PATENT DOCUMENTS

| | | | | |
|---|---|---|---|---|
| WO | WO 2011/057003 A2 * | 5/2011 | ........... | A61K 31/713 |

OTHER PUBLICATIONS

Valadi et al. (Nature Cell Biology, vol. 9, No. 6, 2007, pp. 654-659).*
Crossland et al. (Journal of Immunological Methods, 429, 2016, 39-49).*
Kormelink et al., J Immunol Oct. 15, 2016, 197 (8) 3382-3392.*
Shao et al. (Endocrine (2017) 55:130-138).*
Snowhite et al. (Diabetologia. Aug. 2017 ; 60(8): 1409-1422).*
Dabelea D, Mayer-Davis EJ, Saydah S, et al. (2014) Prevalence of type 1 and type 2 diabetes among children and adolescents from 2001 to 2009. JAMA 311: 1778-1786.
Maahs DM, West NA, Lawrence JM, Mayer-Davis EJ (2010) Chapter 1: Epidemiology of Type 1 Diabetes. Endocrinology and metabolism clinics of North America 39: 481-497.
Eisenbarth GS (1986) Type I diabetes mellitus. A chronic autoimmune disease. The New England journal of medicine 314: 1360-1368.
Atkinson MA, Eisenbarth GS, Michels AW (2014) Type 1 diabetes. Lancet (London, England) 383: 69-82.
Heninger A-K, Eugster A, Kuehn D, et al. (2017) A divergent population of autoantigen-responsive T cells in infants prior to β cell autoimmunity. Science Translational Medicine 9.
Cianciaruso C, Phelps EA, Pasquier M, et al. (2017) Primary Human and Rat beta-Cells Release the Intracellular Autoantigens GAD65, IA-2, and Proinsulin in Exosomes Together With Cytokine-Induced Enhancers of Immunity. Diabetes 66: 460-473.
Sims EK, Lakhter AJ, Anderson-Baucum E, Kono T, Tong X, Evans-Molina C (2017) MicroRNA 21 targets BCL2 mRNA to increase apoptosis in rat and human beta cells. Diabetologia.
Gould SJ, Raposo G (2013) As we wait: coping with an imperfect nomenclature for extracellular vesicles. J Extracell Vesicles 2.
Yanez-Mo M, Siljander PR, Andreu Z, et al. (2015) Biological properties of extracellular vesicles and their physiological functions. J Extracell Vesicles 4: 27066.
Kowal J, Arras G, Colombo M, et al. (2016) Proteomic comparison defines novel markers to characterize heterogeneous populations of extracellular vesicle subtypes. Proceedings of the National Academy of Sciences of the United States of America 113: E968-E977.
Willms E, Johansson HJ, Mäger I, et al. (2016) Cells release subpopulations of exosomes with distinct molecular and biological properties. Scientific Reports 6: 22519.
Chen Y, Pfeifer A Brown Fat-Derived Exosomes: Small Vesicles with Big Impact. Cell Metabolism 25: 759-760.
Rahman MJ, Regn D, Bashratyan R, Dai YD (2014) Exosomes released by islet-derived mesenchymal stem cells trigger autoimmune responses in NOD mice. Diabetes 63: 1008-1020.
Pitt JM, Kroemer G, Zitvogel L (2016) Extracellular vesicles: masters of intercellular communication and potential clinical interventions. The Journal of Clinical Investigation 126: 1139-1143.
Garcia-Contreras M, Brooks RW, Boccuzzi L, Robbins PD, Ricordi C (2017) Exosomes as biomarkers and therapeutic tools for type 1 diabetes mellitus. Eur Rev Med Pharmacol Sci 21: 2940-2956.

(Continued)

*Primary Examiner* — Amy H Bowman
(74) *Attorney, Agent, or Firm* — Barnes & Thornburg LLP

(57) ABSTRACT

Methods and compositions are provided for detecting and/or determining a patient's risk of developing hyperglycemia or type 1 diabetes. The methods are directed to analyzing the miRNA content of extracellular vesicles recovered from said patient.

8 Claims, 10 Drawing Sheets
Specification includes a Sequence Listing.

(56) References Cited

OTHER PUBLICATIONS

Ruan Q, Wang T, Kameswaran V, et al. (2011) The microRNA-21—PDCD4 axis prevents type 1 diabetes by blocking pancreatic β cell death. Proceedings of the National Academy of Sciences 108: 12030-12035.
Roggli E, Britan A, Gattesco S, et al. (2010) Involvement of MicroRNAs in the Cytotoxic Effects Exerted by Proinflammatory Cytokines on Pancreatic β-Cells. Diabetes 59: 978-986.
Roggli E, Gattesco S, Caille D, et al. (2012) Changes in MicroRNA Expression Contribute to Pancreatic β-Cell Dysfunction in Prediabetic NOD Mice. Diabetes 61: 1742-1751.
Seyhan AA, Nunez Lopez YO, Xie H, et al. (2016) Pancreas-enriched miRNAs are altered in the circulation of subjects with diabetes: a pilot cross-sectional study. Scientific Reports 6: 31479.
Hatanaka M, Anderson-Baucum E, Lakhter A, et al. (2017) Chronic high fat feeding restricts islet mRNA translation initiation independently of ER stress via DNA damage and p53 activation. Sci Rep 7: 3758.
Scharfmann R, Pechberty S, Hazhouz Y, et al. (2014) Development of a conditionally immortalized human pancreatic β cell line. The Journal of clinical investigation 124: 2087-2098.
Tersey SA, Nishiki Y, Templin AT, et al. (2012) Islet beta-cell endoplasmic reticulum stress precedes the onset of type 1 diabetes in the nonobese diabetic mouse model. Diabetes 61: 818-827.
Clancy JW, Sedgwick A, Rosse C, et al. (2015) Regulated delivery of molecular cargo to invasive tumour-derived microvesicles. Nature communications 6: 6919.
Thery C, Amigorena S, Raposo G, Clayton A (2006) Isolation and characterization of exosomes from cell culture supernatants and biological fluids. Current protocols in cell biology Chapter 3: Unit 3.22.
Fisher MM, Watkins RA, Blum J, et al. (2015) Elevations in Circulating Methylated and Unmethylated Preproinsulin DNA in New-Onset Type 1 Diabetes. Diabetes 64: 3867-3872.
Prochazka M, Serreze DV, Frankel WN, Leiter EH (1992) NOR/Lt mice: MHC-matched diabetes-resistant control strain for NOD mice. Diabetes 41: 98-106.
Stull ND, Breite A, McCarthy R, Tersey SA, Mirmira RG (2012) Mouse islet of Langerhans isolation using a combination of purified collagenase and neutral protease. Journal of visualized experiments : JoVE.
Osipova J, Fischer D-C, Dangwal S, et al. (2014) Diabetes-Associated MicroRNAs in Pediatric Patients With Type 1 Diabetes Mellitus: A Cross-Sectional Cohort Study. The Journal of Clinical Endocrinology & Metabolism 99: 1661-1665.
Crescitelli R, Lasser C, Szabo TG, et al. (2013) Distinct RNA profiles in subpopulations of extracellular vesicles: apoptotic bodies, microvesicles and exosomes. J Extracell Vesicles 2.
Ha M, Kim VN (2014) Regulation of microRNA biogenesis. Nat Rev Mol Cell Biol 15: 509-524.
Snowhite IV, Allende G, Sosenko J, Pastori RL, Messinger Cayetano S, Pugliese A (2017) Association of serum microRNAs with islet autoimmunity, disease progression and metabolic impairment in relatives at risk of type 1 diabetes. Diabetologia 60: 1409-1422.

Erener S, Mojibian M, Fox JK, Denroche HC, Kieffer TJ (2013) Circulating miR-375 as a Biomarker of β-Cell Death and Diabetes in Mice. Endocrinology 154: 603-608.
Song I, Roels S, Martens GA, Bouwens L (2017) Circulating microRNA-375 as biomarker of pancreatic beta cell death and protection of beta cell mass by cytoprotective compounds. PLoS ONE 12: e0186480.
Guay C, Menoud V, Rome S, Regazzi R (2015) Horizontal transfer of exosomal microRNAs transduce apoptotic signals between pancreatic beta-cells. Cell communication and signaling : CCS 13: 17.
Sheng H, Hassanali S, Nugent C, et al. (2011) Insulinoma-released exosomes or microparticles are immunostimulatory and can activate autoreactive T cells spontaneously developed in nonobese diabetic mice. The Journal of Immunology 187: 1591-1600.
Cantaluppi V, Biancone L, Figliolini F, et al. (2012) Microvesicles derived from endothelial progenitor cells enhance neoangiogenesis of human pancreatic islets. Cell transplantation 21: 1305-1320.
Palmisano G, Jensen SS, Le Bihan M-C, et al. (2012) Characterization of membrane-shed microvesicles from cytokine-stimulated β-cells using proteomics strategies. Molecular & Cellular Proteomics 11: 230-243.
Zhu Q, Kang J, Miao H, et al. (2014) Low-dose cytokine-induced neutral ceramidase secretion from INS-1 cells via exosomes and its anti-apoptotic effect. FEBS Journal 281: 2861-2870.
Vallabhajosyula P, Korutla L, Habertheuer A, et al. (2017) Tissue-specific exosome biomarkers for noninvasively monitoring immunologic rejection of transplanted tissue. The Journal of clinical investigation 127.
Hasilo CP, Negi S, Allaeys I, et al. (2017) Presence of diabetes autoantigens in extracellular vesicles derived from human islets. Sci Rep 7: 5000.
Garcia-Contreras M, Shah SH, Tamayo A, et al. (2017) Plasma-derived exosome characterization reveals a distinct microRNA signature in long duration Type 1 diabetes. Sci Rep 7: 5998.
Turchinovich A, Samatov TR, Tonevitsky AG, Burwinkel B (2013) Circulating miRNAs: cell-cell communication function Front Genet 4: 119.
Erener S, Marwaha A, Tan R, Panagiotopoulos C, Kieffer TJ (2017) Profiling of circulating microRNAs in children with recent onset of type 1 diabetes. JCI Insight 2: e89656.
Nielsen LB, Wang C, Sørensen K, et al. (2012) Circulating Levels of MicroRNA from Children with Newly Diagnosed Type 1 Diabetes and Healthy Controls: Evidence That miR-25 Associates to Residual Beta-Cell Function and Glycaemic Control during Disease Progression. Experimental Diabetes Research 2012: 896362.
Akirav EM, Lebastchi J, Galvan EM, et al. (2011) Detection of β cell death in diabetes using differentially methylated circulating DNA Proceedings of the National Academy of Sciences of the United States of America 108: 19018-19023.
Pesenacker AM, Wang AY, Singh A, et al. (2016) A Regulatory T-Cell Gene Signature Is a Specific and Sensitive Biomarker to Identify Children With New-Onset Type 1 Diabetes. Diabetes 65: 1031.
Krichevsky AM, Gabriely G (2009) miR-21: a small multi-faceted RNA. J Cell Mol Med 13: 39-53.

\* cited by examiner

Circulating EVs miR193 3p Serum EVs

Enrichment of INS mRNA in EVs from human islet supernatant

Circulating INS mRNA following MMTT

SEQUENCE LISTING

```
<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
ctagcttatc agactgatgt tg                                                22
```

EXTRACELLULAR VESICLE RIBONUCLEIC ACID (RNA) CARGO AS A BIOMARKER OF HYPERGLYCEMIA AND TYPE 1 DIABETES

CROSS REFERENCE TO RELATED APPLICATIONS

This application claims priority to the following: U.S. Provisional Patent Application No. 62/619,464 filed on Jan. 19, 2018, the disclosure of which is hereby expressly incorporated by reference in its entirety.

STATEMENT OF GOVERNMENT SUPPORT

This invention was made with government support under DK104166 and DK103983 awarded by National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 588 bytes ACII (Text) file named "2018-075-02_ST25.txt" created on Jan. 7, 2019.

BACKGROUND OF THE DISCLOSURE

The present disclosure relates generally to type 1 diabetes and methods for detecting RNAs. More particularly, the present disclosure relates to methods for detecting RNAs in extracellular vesicles. The present disclosure also relates to methods for identifying a subject as susceptible to hyperglycemia and methods for identifying a subject as susceptible to type 1 diabetes.

The global incidence of type 1 diabetes has been consistently rising by 3-5% a year, impacting millions of people worldwide. Type 1 diabetes develops over time, with progressive dysfunction and destruction of pancreatic beta cells, such that by the time of clinical disease presentation, patients have lost a substantial portion of their functional beta cell mass. Emerging data have suggested that the beta cell itself may be contributing to type 1 diabetes development via activation of intrinsic stress pathways that exacerbate or accelerate autoimmune mediated destruction. These data highlight a need for robust biomarkers of beta cell health to identify and monitor beta cell dysfunction. Such strategies would not only improve our understanding of the contribution of beta cell dysfunction to the natural history of type 1 diabetes but would also enable the detection of developing diabetes, permitting earlier administration of disease modifying therapies.

Accordingly, there exists a need to identify improved biomarkers for the detection of developing type 1 diabetes.

SUMMARY

The present disclosure relates generally to type 1 diabetes and methods for detecting RNAs. More particularly, the present disclosure relates to methods for detecting extracellular vesicle RNA. The present disclosure also relates to methods for identifying a subject as susceptible to hyperglycemia and methods for identifying a subject as susceptible to type 1 diabetes.

In one aspect, the present disclosure is directed to a method of detecting a ribonucleic acid (RNA) in a sample obtained from a subject. The method comprises: obtaining a sample from the subject; and detecting RNA in an extracellular vesicle.

In one aspect, the present disclosure is directed to a method of identifying a subject as susceptible to hyperglycemia, the method comprising: obtaining a sample from the subject; and detecting extracellular vesicle RNA in the sample.

In one aspect, the present disclosure is directed to a method of identifying a subject as susceptible to type 1 diabetes, the method comprising: obtaining a sample from the subject; and detecting extracellular vesicle RNA in the sample.

BRIEF DESCRIPTION OF THE DRAWINGS

(FIGS. 1a, 1d, 1g, 1b, 1e, 1h) MIN6 and EndoC beta cells and (FIGS. 1c, 1f, 1i) human islets were treated with vehicle (white bars/circles) or a mix of IL-113, INFγ, and TNFα (black bars/circles) for 24 h. (FIGS. 1a-1c): miR-21-5p expression was assessed in MIN6 and EndoC cells, and in human islets (n=3-6 for cells and n=10 for human islets). (FIGS. 1d-1f): miR-21-5p levels were assessed in EVs from MIN6 and EndoC cells and human islets treated with vehicle or cytokine mix (n=3-6). (FIGS. 1g-1i): NTA was performed to profile EV particle concentration and size distribution (n=3). (FIGS. 1j-1k): MIN6 and EndoC cells were treated with inflammatory cytokines or cytokines in combination with the pancaspase inhibitor Z-VAD-FMK. Effects on relative levels of EV miR-21-5p were assessed by RT-qPCR. Results displayed as mean±SD;  *$p \leq 0.05$,  **$p \leq 0.01$.  Veh=vehicle, Cyto=cytokines, RQ=relative quantity.

(FIG. 2a) Immunoblot and (FIG. 2b) transmission electron microscopy of EndoC cell derived EVs were used to validate EV isolation by serial ultracentrifugation. (FIGS. 2c-2e): Relative levels of miR-21-5p were assessed by RT-qPCR. (FIGS. 2f-2h): NTA of each ultracentrifugation fraction from EndoC cells was utilized to establish EV quantity and size distribution. (n=3-5) TEM images display representative data from three independent experiments. Scale bars represent 400 nm. Results displayed as mean±SD;  *$p \leq 0.05$,  $p \leq 0.01$,  *$p \leq 0.001$, MV=microvesicles, EXO=exosomes, RQ=relative quantity.

(FIG. 3c) Specificity of EV isolation was validated by WB of total serum and circulating EVs, probed for EV markers CD63 and CD9 and the ER marker calreticulin. (FIG. 3d) Longitudinal weekly serum collections and blood glucose assessments of NOD (n=7-9; black circles) and control NOR (n=5; white circles) mice were performed, starting at 8 weeks of age and until either development of diabetes, or until 20 weeks of age. (FIG. 3e) RT-qPCR was performed to quantify serum EV miR-21-5p in NOD mice relative to controls by age (n=3-9/group). (FIG. 3f) NOD serum EV miR-21-5p relative to age-matched NOR controls was also analyzed with relationship to diabetes onset (defined as first glucose >4.4 mmol/l). NTA of serum EVs in NOD mice showed no significant changes with relation to (FIG. 3g) age or (FIG. 3h) diabetes onset. Results displayed as mean±SD; †p=0.053, *p≤0.05, p≤0.01, *p≤0.001. RQ=relative quantity.

FIG. 4c depicts circulating EV miR-21-5p normalized to total serum miR-21-5p. FIG. 4d depicts NTA to quantify serum EV concentration and size distribution FIG. 4e depicts quantification of total particle concentration in HC and T1D. FIG. 4f depicts quantification of particle size in HC and T1D. FIG. 4g depicts serum EV miR-21-5p normalized to total serum particle number in human HC and T1D. FIG. 4h depicts relative levels of total serum miR-375-5p HC and T1D. FIG. 4i depicts circulating EV miR-375-5p in HC and T1D.

FIG. 4j depicts the relationship between serum EV miR-21-5p and EV miR-375-5p in samples from subjects with type 1 diabetes. FIG. 4k is a representative image of a transmission electron micrograph of EV isolated from serum. Scale bar represents 400 nm. Three independent experiments are shown. Results shown as median±IQR or mean±SEM (FIG. 4d); *p≤0.05, p≤0.01, *p≤0.001 HC=healthy control subjects, T1D=subjects with type 1 diabetes.

FIGS. 8A & 8B provide bar graphs of Enrichment of INS mRNA in microvesicle (MVBs) from human islet supernatant, wherein FIG. 8A represents total RNAs isolated from MVBs and FIG. 8B provides a graph showing the expression of INS in MVBs vs Non-MVB supernatant.

FIG. 11A presents data showing bound EVs was drastically increased for human 3 cells compared to other cell types. FIG. 11B presents data showing miR-21-5p isolated from EVs after cytokines (+) vs. control (−) treatment of the listed cell types.

DETAILED DESCRIPTION

Abbreviations

Figures 1A, 1B, 1C, 1D, 1E, 1F, 1G, 1H, 1I, 1J, 1K:
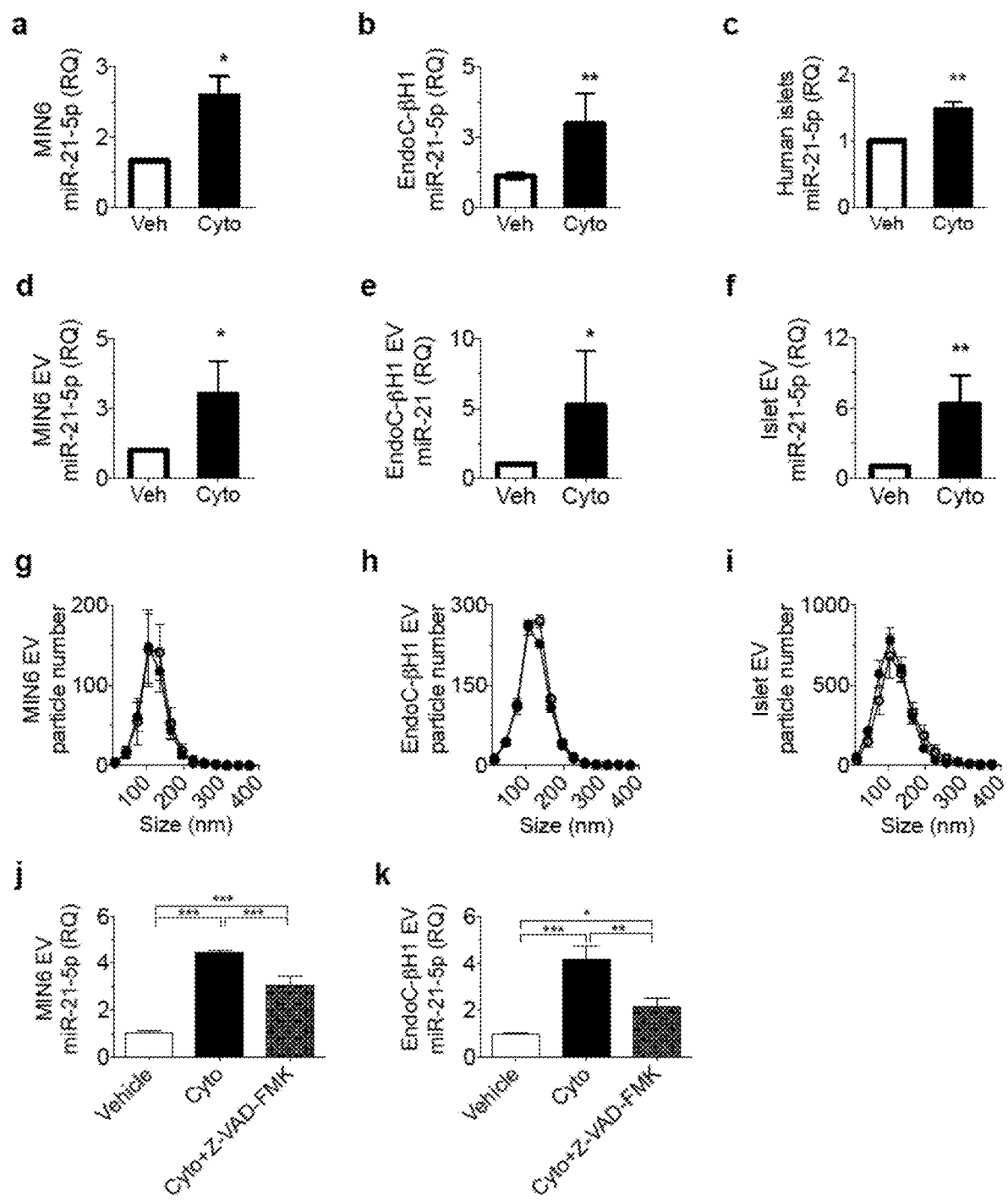
FIGS. 1a-1k depict increased 3 cell EV miR-21-5p cargo by inflammatory cytokines.

EV Extracellular Vesicle
miR-21-5p microRNA-21
FBS fetal bovine serum
NTA Nanoparticle tracking analysis
TEM Transmission electron microscopy
qPCR Quantitative real-time PCR
NOD NOD/LtJ
NOR NOR/LtJ
MV Microvesicle
EXO Exosome
EndoC cells EndoC-βH1 cells

Definitions

Unless defined otherwise, all technical and scientific terms used herein have the same meaning as commonly understood by one of ordinary skill in the art to which the disclosure belongs. In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

The term, "parenteral" means not through the alimentary canal but by some other route such as subcutaneous, intramuscular, intraspinal, or intravenous.

As used herein, the term "purified" and like terms relate to the isolation of a molecule or compound in a form that is substantially free of contaminants normally associated with the molecule or compound in a native or natural environment.

As used herein, the term "purified" does not require absolute purity; rather, it is intended as a relative definition. The term "purified RNA" is used herein to describe an RNA sequence which has been separated from other compounds including, but not limited to polypeptides, lipids and carbohydrates.

The term "isolated" requires that the referenced material be removed from its original environment (e.g., the natural environment if it is naturally occurring). For example, a naturally-occurring nucleic acid present in a living animal is not isolated, but the same nucleic acid, separated from some or all of the coexisting materials in the natural system, is isolated.

As used herein the term "patient" without further designation is intended to encompass any warm blooded vertebrate domesticated animal (including for example, but not limited to livestock, horses, mice, cats, dogs and other pets) and humans.

As used herein, "a subject in need thereof" refers to a subject having, susceptible to or at risk of a specified disease, disorder, or condition. More particularly, in the present disclosure the methods of screening biomarkers are to be used with a subset of subjects who have, are susceptible to or are at an elevated risk for experiencing hyperglycemia and type 1 diabetes. Such subjects can be susceptible to or at elevated risk for hyperglycemia and type 1 diabetes due to family history, age, environment, and/or lifestyle.

Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

As used herein, "susceptible" and "at risk" refer to having little resistance to a certain disease, disorder or condition, including being genetically predisposed, having a family history of, and/or having symptoms of the disease, disorder or condition.

As used herein, "expression level of a biomarker" refers to the process by which a gene product is synthesized from a gene encoding the biomarker as known by those skilled in the art. The gene product can be, for example, RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, enzyme linked immunosorbent assay (ELISA), immunohistochemical staining, in situ hybridization and combinations thereof.

As used herein, "a reference expression level of a biomarker" refers to the expression level of a biomarker established for a subject without hyperglycemia and type 1 diabetes, expression level of a biomarker in a normal/healthy subject without hyperglycemia and type 1 diabetes as determined by one skilled in the art using established methods as described herein, and/or a known expression level of a biomarker obtained from literature. The reference expression level of the biomarker can also refer to the expression level of the biomarker established for any combination of subjects such as a subject without hyperglycemia and type 1 diabetes, expression level of the biomarker in a normal/healthy subject without hyperglycemia and type 1 diabetes, and expression level of the biomarker for a subject without hyperglycemia and type 1 diabetes at the time the sample is obtained from the subject, but who later exhibits hyperglycemia and type 1 diabetes. The reference expression level of the biomarker can also refer to the expression level of the biomarker obtained from the subject to which the method is applied. As such, the change within a subject from visit to visit can indicate an increased or decreased risk for hyperglycemia and type 1 diabetes. For example, a plurality of expression levels of a biomarker can be obtained from a plurality of samples obtained from the same subject and can be used to identify differences between the pluralities of expression levels in each sample. Thus, in some embodiments, two or more samples obtained from the same subject can provide an expression level(s) of a blood biomarker and a reference expression level(s) of the blood biomarker. As further used herein, "a reference expression level of a biomarker" refers to the expression level of a biomarker established for a subject having hyperglycemia and/or type 1 diabetes (including subjects having longstanding type 1 diabetes and subjects having new onset type 1 diabetes).

EMBODIMENTS

In one aspect, the present disclosure is directed to a method of detecting a ribonucleic acid (RNA) in a sample obtained from a subject. The method includes: obtaining a sample from the subject; and detecting a ribonucleic acid (RNA) in an extracellular vesicle.

Suitable RNAs include messenger RNA (mRNA), microRNA (miRNA), long intergenic non-coding RNA (lincRNA), long non-coding RNA (lncRNA), non-coding RNA (ncRNA), non-messenger RNA (nmRNA), small RNA (sRNA), small non-messenger RNA (smnRNA), DNA damage response RNA (DD RNA), extracellular RNA (exRNA), small nuclear RNA (snRNA), small nucleolar RNA (snoRNA), and precursor messenger RNA (pre-mRNA). Suitable microRNAs include miR-155p, miR-146a-5p, miR-205-5p, miR-21-3p, miR-23a-5p, miR-363-3p, miR-431-5p, miR-147b, miR-4521, miR-194-3p, miR-4443, miR-543, miR-1229-3p, miR-7704, miR-29b-1-5p, miR-210-3p, miR-423-5p, miR-483-3p, miR-126-5p, miR-30e-3p, miR-145-5p, miR-145-3p, miR-33a-5p, miR-296-3p, miR-758-5p, miR-665, miR-335-3p, miR-181a-2-3p, miR-1226-3p, miR-802, miR-106a-5p, miR-31-3p, miR-193b-5p, miR-193b-3p, miR-148a-3p, miR-217, miR-216a-5p, miR-216a-3p, miR-21-5p, miR-148a-5p, miR-130b-3p, miR-224-5p, miR-629-5p, miR-876-3p, miR-502-3p, miR-4485, miR-210-5p, miR-124-3p, and combinations thereof. Particularly suitable microRNAs include human miRNAs including hsa-miR-155p, hsa-miR-146a-5p, hsa-miR-205-5p, hsa-miR-21-3p, hsa-miR-23a-5p, hsa-miR-363-3p, hsa-miR-431-5p, hsa-miR-147b, hsa-miR-4521, hsa-miR-194-3p, hsa-miR-4443, hsa-miR-543, hsa-miR-1229-3p, hsa-miR-7704, hsa-miR-29b-1-5p, hsa-miR-210-3p, hsa-miR-423-5p, hsa-miR-483-3p, hsa-miR-126-5p, hsa-miR-30e-3p, hsa-miR-145-5p, hsa-miR-145-3p, hsa-miR-33a-5p, hsa-miR-296-3p, hsa-miR-758-5p, hsa-miR-665, hsa-miR-335-3p, hsa-miR-181a-2-3p, hsa-miR-1226-3p, hsa-miR-802, hsa-miR-106a-5p, hsa-miR-31-3p, hsa-miR-193b-5p, hsa-miR-193b-3p, hsa-miR-148a-3p, hsa-miR-217, hsa-miR-216a-5p, hsa-miR-216a-3p, hsa-miR-21-5p, hsa-miR-148a-5p, hsa-miR-130b-3p, hsa-miR-224-5p, hsa-miR-629-5p, hsa-miR-876-3p, hsa-miR-502-3p, hsa-miR-4485, hsa-miR-210-5p, hsa-miR-124-3p, and combinations thereof.

Extracellular vesicles (EVs) are membrane bound nanoparticles released from all cell types that function in intercellular communication. EVs are often broadly classified into three categories, exosomes, microvesicles, and apoptotic bodies, based on their size, cellular origin and formation mechanism. Suitable extracellular vesicles to detect RNA include circulating extracellular vesicles, beta cell extracellular vesicles, islet cell extracellular vesicles, exosomes and apoptotic bodies, and combinations thereof. Large extracellular vesicles can range from about 5 µm to about 12 µm in diameter. Apoptotic bodies can range from about 1 µm to about 5 µm in diameter. Microvesicles can range from about 100 nm to about 1 μm in diameter. Exosomes can range from about 30 nm to about 100 nm in diameter.

In accordance with one embodiment a method is provided for isolating and detecting miRNA associated with extracellular vesicles of patients. In one embodiment the extracellular vesicles are isolated form a blood sample including a serum sample, using centrifugation techniques known to those skilled in the art. In a further embodiment the method includes the use of an extracellular vesicle marker of the extracellular vesicle for isolating the vesicles. Suitable extracellular vesicle markers include CD9 and CD63.

The method can further include isolating an extracellular vesicle from the sample. Suitable extracellular vesicles to isolate include circulating extracellular vesicles, beta cell extracellular vesicles, islet cell extracellular vesicles, exosomes and apoptotic bodies, and combinations thereof.

Suitable methods for isolating extracellular vesicles include commercially available reagents such as, for example, EXOQUICK TC reagent (commercially available from System Biosciences, Palo Alto, Calif.) and size separation methods such as centrifugation A particularly suitable isolation method includes sequential centrifugation such as by centrifuging a sample at 800 g for a desired amount of time, collecting the pellet containing cells and cellular debris and (first) supernatant, centrifuging the (first) supernatant at 2,000 g for a desired time, collecting the pellet containing large extracellular vesicles and apoptotic bodies and (second) supernatant). The sequential centrifugation method can further include centrifuging the (second) supernatant at 10,000 g, collecting the pellet containing microvesicles and (third) supernatant). The sequential centrifugation method can further include centrifuging the (third) supernatant at 100,000 g, collecting the pellet containing exosomes (ranging from about 30 nm to about 200 nm in diameter) and (fourth) supernatant). The sequential centrifugation method can further include washing each of the pellets including the extracellular vesicles (i.e., large extracellular vesicles and apoptotic bodies, microvesicles, and exosomes) such as in phosphate buffered saline followed by centrifugation at the appropriate gravitational force and collecting the pellet containing the extracellular vesicles. Isolation, purity, concentration, size, size distribution, and combinations thereof of the extracellular vesicles following each centrifugation step can be confirmed using methods such as nanoparticle tracking, transmission electron microscopy, immunoblotting, and combinations thereof. Nanoparticle tracking (NTA) to analyze extracellular vesicles such as for concentration and size can be performed by dynamic light scattering using commercially available instruments such as ZETAVIEW (commercially available from ParticleMetrix, Meerbusch, Germany). Data acquisition can suitably be performed at room temperature. NTA measurements preferably are recorded and analyzed at multiple positions per sample using computer software such as ZETAVIEW Analyze software (commercially available from ParticleMetrix). Following isolation, the method can further include detecting an extracellular vesicle marker of the extracellular vesicle. Suitable extracellular vesicle markers include CD9, CD63, CD81, LAPM1, TSG101, and combinations thereof. Suitable samples include whole blood, plasma, serum, culture media, and combinations thereof.

The method can further include detecting circulating RNAs including messenger RNA (mRNA), microRNA (miRNA), long intergenic non-coding RNA (lincRNA), long non-coding RNA (lncRNA), non-coding RNA (ncRNA), non-messenger RNA (nmRNA), small RNA (sRNA), small non-messenger RNA (smnRNA), DNA damage response RNA (DD RNA), extracellular RNA (exRNA), small nuclear RNA (snRNA), small nucleolar RNA (snoRNA), and precursor messenger RNA (pre-mRNA). Particularly suitable circulating miRNAs include miR-155p, miR-146a-5p, miR-205-5p, miR-21-3p, miR-23a-5p, miR-363-3p, miR-431-5p, miR-147b, miR-4521, miR-194-3p, miR-4443, miR-543, miR-1229-3p, miR-7704, miR-29b-1-5p, miR-210-3p, miR-423-5p, miR-483-3p, miR-126-5p, miR-30e-3p, miR-145-5p, miR-145-3p, miR-33a-5p, miR-296-3p, miR-758-5p, miR-665, miR-335-3p, miR-181a-2-3p, miR-1226-3p, miR-802, miR-106a-5p, miR-31-3p, miR-193b-5p, miR-193b-3p, miR-148a-3p, miR-217, miR-216a-5p, miR-216a-3p, miR-21-5p, miR-148a-5p, miR-130b-3p, miR-224-5p, miR-629-5p, miR-876-3p, miR-502-3p, miR-4485, miR-210-5p, miR-124-3p, miR-217, and combinations thereof.

In one embodiment a method of detecting a ribonucleic acid (RNA) in a sample obtained from a subject is provided wherein the method comprises obtaining a sample from the subject; and detecting RNA in an extracellular vesicle, optionally wherein the extracellular vesicle is a circulating extracellular vesicle. In one embodiment the extracellular vesicle comprises a beta cell extracellular vesicle and/or an islet cell extracellular vesicle. In one embodiment the extracellular vesicle comprises an exosome and an apoptotic body. In accordance with one embodiment the method comprises detecting an extracellular vesicle marker of the extracellular vesicle, optionally wherein the extracellular vesicle marker comprises CD9 and CD63.

In accordance with one embodiment a method is provided for isolating circulating extracellular vesicles from a patient's blood stream, wherein the extracellular vesicles are isolated and size selected based on ultracentrifugation. In one embodiment the extracellular vesicles are further selected based on detection of an extracellular vesicle marker selected from CD9 or CD63. In one embodiment the patient sample is chosen from whole blood, serum, or plasma.

In one embodiment a method is provided for detecting circulating extracellular vesicle (EV) that comprise miR-21-5p: "EV miR-21-5p". The detection of elevated EV miR-21-5p in a patient's blood relative to control samples is associated with a higher risk of the development of type 1 diabetes and/or hyperglycemia. In one embodiment the method further comprises detecting blood glucose levels of said patient. In one embodiment a method of identifying a subject as susceptible to hyperglycemia or development of type 1 diabetes, the method comprising: obtaining a sample; and analyzing the extracellular vesicle RNA. In one embodiment, the method of identifying a subject as susceptible to hyperglycemia or development of type 1 diabetes comprises obtaining a first sample and at least a second sample from the subject and wherein the detecting step comprises detecting extracellular vesicle RNA in the first sample and detecting extracellular vesicle RNA in the second sample, wherein an increase in the extracellular vesicle RNA content of the second sample is predictive of hyperglycemia or development of type 1 diabetes. In one embodiment the extracellular vesicle is a circulating extracellular vesicle, including for example an exosome or an apoptotic body, optionally derived from a beta cell extracellular vesicle, an islet cell extracellular vesicle. In one embodiment the method of isolating the extracellular vesicle includes the use of an extracellular vesicle marker such as CD9 and CD63.

In accordance with one embodiment a method of identifying a subject as susceptible to type 1 diabetes is provided.

The method comprises obtaining a sample from the subject and detecting extracellular vesicle RNA in the sample. In one embodiment the method further comprises detecting circulating RNA and in a further embodiment the method includes detecting the blood glucose level. In one embodiment the method comprises obtaining a first sample and at least a second sample from the patient wherein a predetermined time is set between the collection of the first and second sample is selected from 1, 2, 3, 4, 5, 6, or 7 days, 1 month, 2 months, 3 months or 1 year. In one embodiment multiple samples are collected over the course of 1, 2, 3, 4, or 5 years. In this embodiment the detecting step comprises analyzing extracellular vesicle RNA in the first sample and analyzing extracellular vesicle RNA in the second sample wherein the subject is identified as susceptible to type 1 diabetes when the extracellular vesicle RNA detected in the second sample is increased when compared to the extracellular vesicle RNA detected in the first sample. In one embodiment the extracellular vesicle is a circulating extracellular vesicle, optionally wherein the extracellular vesicle comprises an exosome and an apoptotic body, and optionally is a beta cell extracellular vesicle or an islet cell extracellular vesicle.

The method can further include determining blood glucose or insulin levels in the sample. In one embodiment the method further includes detecting a protein in an extracellular vesicle, optionally wherein the extracellular vesicle comprises an exosome and an apoptotic body, and optionally wherein the extracellular vesicle is a beta cell extracellular vesicle or an islet cell extracellular vesicle.

In one aspect, the present disclosure is directed to a method of identifying a subject as susceptible to hyperglycemia, the method comprising: obtaining a sample; and detecting extracellular vesicle RNA.

Suitable RNA includes messenger RNA (mRNA), microRNA (miRNA), long intergenic non-coding RNA (lincRNA), long non-coding RNA (lncRNA), non-coding RNA (ncRNA), non-messenger RNA (nmRNA), small RNA (sRNA), small non-messenger RNA (smnRNA), DNA damage response RNA (DD RNA), extracellular RNA (exRNA), small nuclear RNA (snRNA), small nucleolar RNA (snoRNA), and precursor messenger RNA (pre-mRNA). Particularly suitable miRNAs include miR-155p, miR-146a-5p, miR-205-5p, miR-21-3p, miR-23a-5p, miR-363-3p, miR-431-5p, miR-147b, miR-4521, miR-194-3p, miR-4443, miR-543, miR-1229-3p, miR-7704, miR-29b-1-5p, miR-210-3p, miR-423-5p, miR-483-3p, miR-126-5p, miR-30e-3p, miR-145-5p, miR-145-3p, miR-33a-5p, miR-296-3p, miR-758-5p, miR-665, miR-335-3p, miR-181a-2-3p, miR-1226-3p, miR-802, miR-106a-5p, miR-31-3p, miR-193b-5p, miR-193b-3p, miR-148a-3p, miR-217, miR-216a-5p, miR-216a-3p, miR-21-5p, miR-148a-5p, miR-130b-3p, miR-224-5p, miR-629-5p, miR-876-3p, miR-502-3p, miR-4485, miR-210-5p, miR-124-3p, miR-217, and combinations thereof. Particularly suitable microRNAs include human miRNAs including hsa-miR-155p, hsa-miR-146a-5p, hsa-miR-205-5p, hsa-miR-21-3p, hsa-miR-23a-5p, hsa-miR-363-3p, hsa-miR-431-5p, hsa-miR-147b, hsa-miR-4521, hsa-miR-194-3p, hsa-miR-4443, hsa-miR-543, hsa-miR-1229-3p, hsa-miR-7704, hsa-miR-29b-1-5p, hsa-miR-210-3p, hsa-miR-423-5p, hsa-miR-483-3p, hsa-miR-126-5p, hsa-miR-30e-3p, hsa-miR-145-5p, hsa-miR-145-3p, hsa-miR-33a-5p, hsa-miR-296-3p, hsa-miR-758-5p, hsa-miR-665, hsa-miR-335-3p, hsa-miR-181a-2-3p, hsa-miR-1226-3p, hsa-miR-802, hsa-miR-106a-5p, hsa-miR-31-3p, hsa-miR-193b-5p, hsa-miR-193b-3p, hsa-miR-148a-3p, hsa-miR-217, hsa-miR-216a-5p, hsa-miR-216a-3p, hsa-miR-21-5p, hsa-miR-148a-5p, hsa-miR-130b-3p, hsa-miR-224-5p, hsa-miR-629-5p, hsa-miR-876-3p, hsa-miR-502-3p, hsa-miR-4485, hsa-miR-210-5p, hsa-miR-124-3p, and combinations thereof. In one embodiment the method comprises detecting circulating extracellular vesicles comprising miR-21-5p, wherein the method comprises obtaining a patient blood sample, isolating the extracellular vesicles and detecting and/or quantitating the miR-21-5p associated with the extracellular vesicles comprising miR-21-5p. In one embodiment the method further comprises analyzing additional miRNAs associated with the extracellular vesicles. In one embodiment the extracellular vesicles are exosomes having a size range from about 30 nm to about 100 nm in diameter, or about 30 nm to about 60 nm in diameter. In one embodiment the method further comprises detecting and/or quantitating mRNAs selected from the group consisting of miR-217 and miR193-3p.

The method can include obtaining a plurality of samples from the subject and detecting extracellular vesicle RNA in the plurality of samples. The plurality of samples can be obtained sequentially over any desired period of time. Suitable periods of time can include hourly, daily, weekly, monthly and combinations thereof. For example, the method can include obtaining a first sample and at least a second sample from the subject wherein the detecting comprises detecting extracellular vesicle RNA in the first sample and detecting extracellular vesicle RNA in the second sample. The method can include obtaining a first sample, at least a second sample from the subject, and at least a third sample from the subject and wherein the detecting comprises detecting extracellular vesicle RNA in the first sample, detecting extracellular vesicle RNA in the second sample, and detecting extracellular vesicle RNA in the third sample. Similarly, at least a fourth sample, at least a fifth sample, etc. can be obtained and extracellular vesicle RNA can be detected in each of the samples. Levels of extracellular vesicle RNA from each sample can be compared to each of the other samples (e.g., the first, the second, the third, etc.).

Suitable extracellular vesicles to detect RNA include circulating extracellular vesicles, beta cell extracellular vesicles, islet cell extracellular vesicles, exosomes and apoptotic bodies, and combinations thereof, as described herein.

In one embodiment, the method includes detecting extracellular vesicle microRNA 21 (miR-21-5p). The subject is identified as susceptible to hyperglycemia when the extracellular vesicle microRNA 21 (miR-21-5p) detected in the sample obtained from the subject is increased (i.e., greater than) as compared to a reference extracellular vesicle microRNA 21 (miR-21-5p) expression level. In one embodiment, the reference extracellular vesicle microRNA 21 (miR-21-5p) expression level is obtained from the subject. In another embodiment, the reference extracellular vesicle microRNA 21 (miR-21-5p) expression level is obtained from a subject without hyperglycemia.

Suitable extracellular vesicles to detect RNA include circulating extracellular vesicles, beta cell extracellular vesicles, islet cell extracellular vesicles, exosomes and apoptotic bodies, and combinations thereof, as described herein.

The method can further include detecting an extracellular vesicle marker of the extracellular vesicle. Suitable extracellular vesicle markers include CD9, CD63, CD81, LAPM1, TSG101, and combinations thereof.

The method can further include isolating an extracellular vesicle from the sample, as described herein. Isolation of the extracellular vesicle can be conducted by ultracentrifugation as described herein. In one embodiment a ligand that specifically binds to exosomes is used to precipitate exosomes.

For example, the commercially available ExoQuick TC reagent system (System Biosciences, Palo Alto, Calif.) can be used. Suitable extracellular vesicles for use in the presently disclosed methods include circulating extracellular vesicles, beta cell extracellular vesicles, islet cell extracellular vesicles, exosomes and apoptotic bodies, and combinations thereof, as described herein.

Following isolation, the method can further include detecting an extracellular vesicle marker of the extracellular vesicle. Suitable extracellular vesicle markers include CD9, CD63, CD81, LAPM1, TSG101, and combinations thereof. Suitable samples include whole blood, plasma, serum, culture media, and combinations thereof.

The method can further include detecting circulating RNA. Suitable circulating RNA includes messenger RNA (mRNA), microRNA (miRNA), long intergenic non-coding RNA (lincRNA), long non-coding RNA (lncRNA), non-coding RNA (ncRNA), non-messenger RNA (nmRNA), small RNA (sRNA), small non-messenger RNA (smnRNA), DNA damage response RNA (DD RNA), extracellular RNA (exRNA), small nuclear RNA (snRNA), small nucleolar RNA (snoRNA), and precursor messenger RNA (pre-mRNA). Particularly suitable circulating miRNAs include miR-155p, miR-146a-5p, miR-205-5p, miR-21-3p, miR-23a-5p, miR-363-3p, miR-431-5p, miR-147b, miR-4521, miR-194-3p, miR-4443, miR-543, miR-1229-3p, miR-7704, miR-29b-1-5p, miR-210-3p, miR-423-5p, miR-483-3p, miR-126-5p, miR-30e-3p, miR-145-5p, miR-145-3p, miR-33a-5p, miR-296-3p, miR-758-5p, miR-665, miR-335-3p, miR-181a-2-3p, miR-1226-3p, miR-802, miR-106a-5p, miR-31-3p, miR-193b-5p, miR-193b-3p, miR-148a-3p, miR-217, miR-216a-5p, miR-216a-3p, miR-21-5p, miR-148a-5p, miR-130b-3p, miR-224-5p, miR-629-5p, miR-876-3p, miR-502-3p, miR-4485, miR-210-5p, miR-124-3p, miR-217, and combinations thereof. Particularly suitable microRNAs include human miRNAs including hsa-miR-155p, hsa-miR-146a-5p, hsa-miR-205-5p, hsa-miR-21-3p, hsa-miR-23a-5p, hsa-miR-363-3p, hsa-miR-431-5p, hsa-miR-147b, hsa-miR-4521, hsa-miR-194-3p, hsa-miR-4443, hsa-miR-543, hsa-miR-1229-3p, hsa-miR-7704, hsa-miR-29b-1-5p, hsa-miR-210-3p, hsa-miR-423-5p, hsa-miR-483-3p, hsa-miR-126-5p, hsa-miR-30e-3p, hsa-miR-145-5p, hsa-miR-145-3p, hsa-miR-33a-5p, hsa-miR-296-3p, hsa-miR-758-5p, hsa-miR-665, hsa-miR-335-3p, hsa-miR-181a-2-3p, hsa-miR-1226-3p, hsa-miR-802, hsa-miR-106a-5p, hsa-miR-31-3p, hsa-miR-193b-5p, hsa-miR-193b-3p, hsa-miR-148a-3p, hsa-miR-217, hsa-miR-216a-5p, hsa-miR-216a-3p, hsa-miR-21-5p, hsa-miR-148a-5p, hsa-miR-130b-3p, hsa-miR-224-5p, hsa-miR-629-5p, hsa-miR-876-3p, hsa-miR-502-3p, hsa-miR-4485, hsa-miR-210-5p, hsa-miR-124-3p, and combinations thereof.

The method can include obtaining a plurality of samples from the subject and detecting extracellular vesicle RNA in the plurality of samples. The plurality of samples can be obtained sequentially over any desired period of time. Suitable periods of time can include hourly, daily, weekly, monthly and combinations thereof. For example, the method can include obtaining a first sample and at least a second sample from the subject and wherein the detecting comprises detecting extracellular vesicle RNA in the first sample and detecting extracellular vesicle microRNA 21 (miR-21-5p) in the second sample. The method can include obtaining a first sample, at least a second sample from the subject, and at least a third sample from the subject and wherein the detecting comprises detecting extracellular vesicle RNA in the first sample, detecting extracellular vesicle RNA in the second sample, and detecting extracellular vesicle RNA in the third sample. Similarly, at least a fourth sample, at least a fifth sample, etc. can be obtained and extracellular vesicle RNA can be detected in each of the samples. Levels of extracellular vesicle RNA from each sample can be compared to each of the other samples (e.g., the first, the second, the third, etc.).

In one embodiment, the method includes detecting extracellular vesicle microRNA 21 (miR-21-5p). The subject is identified as susceptible to type 1 diabetes when the extracellular vesicle microRNA 21 (miR-21-5p) detected in the sample obtained from the subject is increased (i.e., greater than) as compared to a reference extracellular vesicle microRNA 21 (miR-21-5p) expression level. In one embodiment, the reference extracellular vesicle microRNA 21 (miR-21-5p) expression level is obtained from the subject. In another embodiment, the reference extracellular vesicle microRNA 21 (miR-21-5p) expression level is obtained from a subject without type 1 diabetes.

Suitable extracellular vesicles to detect RNA include circulating extracellular vesicles, beta cell extracellular vesicles, islet cell extracellular vesicles, exosomes and apoptotic bodies, and combinations thereof, as described herein. The method can further include detecting an extracellular The method can further include analyzing blood glucose levels in the sample. The method can further include detecting extracellular vesicle proinsulin protein. In one aspect, the present disclosure is directed to a method of identifying a subject as susceptible to type 1 diabetes. The method includes: obtaining a sample; and detecting extracellular vesicle RNA.

Suitable RNA includes messenger RNA (mRNA), microRNA (miRNA), long intergenic non-coding RNA (lincRNA), long non-coding RNA (lncRNA), non-coding RNA (ncRNA), non-messenger RNA (nmRNA), small RNA (sRNA), small non-messenger RNA (smnRNA), DNA damage response RNA (DD RNA), extracellular RNA (exRNA), small nuclear RNA (snRNA), small nucleolar RNA (snoRNA), and precursor messenger RNA (pre-mRNA). Particularly suitable miRNAs include miR-155p, miR-146a- vesicle marker of the extracellular vesicle. Suitable extracellular vesicle markers include CD9, CD63, CD81, LAPM1, TSG101, and combinations thereof.

The method can further include isolating an extracellular vesicle from the sample, as described herein. Suitable extracellular vesicles to isolate include circulating extracellular vesicles, beta cell extracellular vesicles, islet cell extracellular vesicles, exosomes and apoptotic bodies, and combinations thereof, as described herein.

Following isolation, the method can further include detecting an extracellular vesicle marker of the extracellular vesicle. Suitable extracellular vesicle markers include CD9, CD63, CD81, LAPM1, TSG101, and combinations thereof. Suitable samples include whole blood, plasma, serum, culture media, and combinations thereof.

The method can further include detecting circulating RNA including messenger RNA (mRNA), microRNA (miRNA), long intergenic non-coding RNA (lincRNA), long non-coding RNA (lncRNA), non-coding RNA (ncRNA), non-messenger RNA (nmRNA), small RNA (sRNA), small non-messenger RNA (smnRNA), DNA damage response RNA (DD RNA), extracellular RNA (exRNA), small nuclear RNA (snRNA), small nucleolar RNA (snoRNA), and precursor messenger RNA (pre-mRNA). Particularly suitable circulating miRNAs include miR-155p, miR-146a-5p, miR-205-5p, miR-21-3p, miR-23a-5p, miR-363-3p, miR-431-5p, miR-147b, miR-4521, miR-194-3p, miR-4443, miR-543, miR-1229-3p, miR-7704, miR-29b-1-5p, miR-210-3p, miR-423-5p, miR-483-3p, miR-126-5p, miR-30e-3p, miR-145-5p, miR-145-3p, miR-33a-5p, miR-296-3p, miR-758-5p, miR-665, miR-335-3p, miR-181a-2-3p, miR-1226-3p, miR-802, miR-106a-5p, miR-31-3p, miR-193b-5p, miR-193b-3p, miR-148a-3p, miR-217, miR-216a-5p, miR-216a-3p, miR-21-5p, miR-148a-5p, miR-130b-3p, miR-224-5p, miR-629-5p, miR-876-3p, miR-502-3p, miR-4485, miR-210-5p, miR-124-3p, miR-217, and combinations thereof. Particularly suitable microRNAs include human miRNAs including hsa-miR-155p, hsa-miR-146a-5p, hsa-miR-205-5p, hsa-miR-21-3p, hsa-miR-23a-5p, hsa-miR-363-3p, hsa-miR-431-5p, hsa-miR-147b, hsa-miR-4521, hsa-miR-194-3p, hsa-miR-4443, hsa-miR-543, hsa-miR-1229-3p, hsa-miR-7704, hsa-miR-29b-1-5p, hsa-miR-210-3p, hsa-miR-423-5p, hsa-miR-483-3p, hsa-miR-126-5p, hsa-miR-30e-3p, hsa-miR-145-5p, hsa-miR-145-3p, hsa-miR-33a-5p, hsa-miR-296-3p, hsa-miR-758-5p, hsa-miR-665, hsa-miR-335-3p, hsa-miR-181a-2-3p, hsa-miR-1226-3p, hsa-miR-802, hsa-miR-106a-5p, hsa-miR-31-3p, hsa-miR-193b-5p, hsa-miR-193b-3p, hsa-miR-148a-3p, hsa-miR-217, hsa-miR-216a-5p, hsa-miR-216a-3p, hsa-miR-21-5p, hsa-miR-148a-5p, hsa-miR-130b-3p, hsa-miR-224-5p, hsa-miR-629-5p, hsa-miR-876-3p, hsa-miR-502-3p, hsa-miR-4485, hsa-miR-210-5p, hsa-miR-124-3p, and combinations thereof.

The method can further include analyzing blood glucose levels in the sample.

The method can further include detecting extracellular vesicle proinsulin protein.

EXAMPLE 1

Materials and Methods
Culture of Cells and Human Islets.
MIN6 cells, originally obtained from J. Miyazaki, were cultured as described previously, but with the use of EV-depleted fetal bovine serum (FBS) (ThermoFisher, Waltham, Mass.). EndoC-βH1 (EndoC) cells, obtained from Raphael Scharfmann, were cultured in serum-free media, as previously described in Scharfmann R et al. ((2014) The Journal of clinical investigation 124: 2087-2098). Human islets were received through the Integrated Islet Distribution Program, which is exempt from IRB approval, and cultured in Standard Islet Medium (Prodo Labs, Aliso Viejo, Calif.) supplemented with Human AB Serum (Prodo), Glutamine and Glutathione (Prodo), and 10 µg/ml ciprofloxacin (Corning, Corning, N.Y.), and depleted of EVs by overnight ultracentrifugation. The authenticity of cell lines was verified through maintenance of glucose-stimulated insulin secretion. Cells were routinely tested for *mycoplasma* with QuickTest *Mycoplasma* Detection Kit (Biotool, Houston, Tex.). Absence of EVs in the media prior to culture was verified by nanoparticle tracking analysis (NTA). To model the inflammatory milieu of type 1 diabetes, samples were exposed to cytokine mix consisting of 5 ng/ml IL-113, 100 ng/ml IFN-γ and 10 ng/ml TNF-α (RnD Systems, Minneapolis, Minn.) for 24 hours as described previously [Sims et al. (2017) MicroRNA 21 targets BCL2 mRNA to increase apoptosis in rat and human beta cells. Diabetologia; Tersey et al. (2012) Diabetes 61: 818-827). To inhibit cytokine-induced apoptosis, 25 µmol/l of the pan-Caspase inhibitor z-VAD-fmk (RnD Systems) was added to the cells concurrently with cytokines. Results presented represent at least 3 independent experiments.

Isolation of Extracellular Vesicles.
Total EVs were isolated from culture media using ExoQuick TC reagent (System Biosciences, Palo Alto, Calif.) and circulating EVs were isolated from 50 µL of serum using ExoQuick reagent (System Biosciences) following manufacturer's guidelines. Sequential ultracentrifugation was utilized to separate EVs by size. The samples were centrifuged at 800 g for 15 minutes to remove dead cells and cellular debris, after which the supernatant was centrifuged at 2,000 g to pellet large EVs/apoptotic bodies. 10,000 g centrifugation of the supernatant from the previous step was utilized to collect microvesicles, and the resulting supernatant was centrifuged at 100,000 g to pellet the exosomes. EVs collected at each step were washed in PBS following described protocols and collected by centrifugation at appropriate speed (Clancy et al. (2015) Nature communications 6: 6919; Thery et al. (2006) Current protocols in cell biology Chapter 3: Unit 3.22). The remaining supernatant was also retained for analysis. Isolation and relative purity of the EVs were confirmed by nanoparticle tracking analysis (NTA), transmission electron microscopy (TEM), and immunoblot.

PCR.
RNA isolation and reverse transcription were performed using miRNeasy and miScript II RT kits according to the manufacturer's instructions (Qiagen, Valencia, Calif.). Where applicable, RNA integrity was determined with Agilent Small RNA kit using Bioanalyzer instrument (Agilent Technologies, Santa Clara, Calif., USA). Quantitative real-time PCR (PCR) was performed using the SooFast EvaGreen Supermix (BioRad, Hercules, Calif.) and a Mastercycler ep realplex instrument (Eppendorf, Happauge, N.Y.). Due to low concentrations, droplet digital PCR (ddPCR) was performed as previously described to quantify serum EV miR-21-3p (Fisher et al. (2015) Diabetes 64: 3867-3872). Primer for RNU6-1 was purchased from Sigma, for miR-21-3p, miR-375-5p, and the *C. elegans* miR-39 spike-in control from Qiagen, and the following primer sequence was used to amplify miR-21-5p: CTAGCT-TATCAGACTGATGTTG (SEQ ID NO:1). Qiagen's universal primer was used as the reverse primer in all reactions. Relative miRNA levels from EV isolates were established against *C. elegans* miR-39 mimic spike-in control (Qiagen), and from cells and tissues relative to RNU6-1, using the ΔΔCq method.

Immunoblot Analysis.

Immunoblot analysis was performed as described previously (Sims et al. (2017) Diabetologia). 1:1000 dilutions of antibodies against calreticulin, CD9 (10292-1-AP and 20597-1-AP, ProteinTech (Rosemon, Ill.)), and CD63 (ABIN1440014, Antibodies-Online (Atlanta, Ga.)) were used for primary detection. Fluorescently labelled secondary antibodies (Jackson ImmunoResearch, West Grove, Pa.) were used in 1:20,000 dilution. Signal detection was conducted on a LI-COR Odyssey imager (LI-COR Biosciences, Lincoln, Nebr.).

Nanoparticle Tracking Analysis (NTA).

Samples enriched for EVs of interest were analyzed for concentration and size distribution with dynamic light scattering using the ZETAVIEW instrument (ParticleMetrix, Meerbusch, Germany). All data acquisition was conducted at room temperature. NTA measurements were recorded and analyzed at 11 positions per sample with ZETAVIEW Analyze software (ParticleMetrix).

Transmission Electron Microscope (TEM) Imaging.

EV-enriched sample preparations were fixed in EM-grade fixative containing 2% (wt/vol) glutaraldehyde and 2% (wt/vol) paraformaldehyde in 0.1M buffered phosphate for at least 30 mins at 4° C. After fixation, samples were placed on 200 mesh silicon monoxide formvar coated grids and stained with NanoVan (Nanoprobes, Yaphank, N.Y.). Images were taken on an FEI Technai G2 Spirit TEM microscope (FEI, Houston, Tex.).

Animal Studies.

8-week female NOD/LtJ (NOD) and NOR/LtJ (NOR) control mice (The Jackson Laboratory, Bar Harbor, Mich.) were followed with weekly blood glucose measurements and serum collections until the onset of diabetes (defined as first of two consecutive blood glucose values >4.4 mmol/l) (Prochazka et al. (1992) Diabetes 41: 98-106). All mice were euglycaemic and test naïve at initial evaluation. Non-diabetic NOD mice were followed until 20 weeks of age to rule out development of diabetes. Terminal serum was collected and islets were isolated as previously described (Stull et al. (2012) Journal of visualized experiments: JoVE). For islet isolation and terminal serum collection, a sample size of 5 NOR and 4 NOD mice were used. Sample sizes of n=5 for NOR controls and n=7-9 (depending on time to diabetes) for NOD mice were chosen for longitudinal experiments because of anticipated variability in prediabetic mice. Blood collection for serum isolation and glucose measurements were done via tail vein nick. Blood glucose was measured using AlphaTRAK glucometer (Abbott Laboratories, Abbott Park, Ill.) following manufacturer's instructions. Serum samples were isolated using Microvette CB 300 system for capillary blood collection (Sarstedt, Numbrecht, Germany). Pancreatic islets were isolated using collagenase digestion as previously described (Tersey et al. (2012) Diabetes 61: 818-827). Animals were maintained within the Indiana University Laboratory Animal Resource Center under pathogen-free conditions, in accordance with the Guide for the Care and Use of Laboratory Animals. All mice were kept in a standard light-dark cycle with ad libitum access to chow and water. All protocols were approved by the Indiana University School of Medicine Institutional Animal Care and Use Committee.

Human Subjects.

Approval was by the Indiana University Institutional Review Board. Informed consent was obtained from parents with assent from children as required. Random serum samples were obtained from 19 pediatric individuals diagnosed with type 1 diabetes by a pediatric endocrinologist within 3 days of clinical diagnosis. $HbA_{1c}$ levels were measured at diagnosis using either the BayerA1cNow system or the Bayer DCA 2000 (Tarrytown, N.Y.). Samples were collected in serum separator tubes and serum was isolated by centrifugation and stored at −80° C. Exclusion criteria included diabetic ketoacidosis requiring an intensive care unit stay, diabetes other than type 1 diabetes, history of prior chronic illness known to affect glucose metabolism, or use of medications known to affect glucose metabolism. Serum from 16 healthy nondiabetic pediatric control individuals was obtained from a biorepository at Indiana University School of Medicine. All available T1D and pediatric samples were assayed in this analysis. All samples were analyzed simultaneously by blinded laboratory personnel.

Statistical Analysis.

GraphPad Prism 7 (GraphPad Software, La Jolla, Calif.) was used for statistical analyses. Significance was assessed by a 2-tailed Student's t test or Mann-Whitney U test (for nonparametric distributions), 1-way ANOVA with Holm-Sidak's multiple comparisons test, or 2-way ANOVA with Sidak's multiple comparisons test for analysis of more than 2 groups. Spearman's correlation analyses were used to measure monotonic relationships. p values were considered statistically significant if <0.05.

Results

In this Example, Beta cell EV miR-21-5p release after inflammatory cytokine exposure was determined. Increased beta cell miR-21-5p expression after treatment with an inflammatory cytokine mix to model the type 1 diabetes inflammatory milieu has been reported (Sims et al. (2017) Diabetologia; Roggli et al. (2010) Diabetes 59: 978-986). Consistent with this, a 1.5-3-fold increase in miR-21-5p expression was detected in MIN6 mouse insulinoma beta cells, EndoC human beta cells, and human islets after 24-hour treatment with IL-11, INFγ, and TNFα (FIGS. 1a-1c). To determine whether this model of pro-inflammatory cytokine stress increases beta cell EV miR-21-5p, miR-21-5p was quantified in EVs from MIN6 cells, EndoC cells, and human islets after treatment with 24 hours of cytokine mix (FIGS. 1d-f). Cytokine exposure induced a 3-6-fold increase in total EV miR-21-5p, indicating a selective enrichment of EV miR-21-5p in response to cytokines, rather than a non-specific reflection of cytokine-induced increases in intracellular miR-21-5p.

To understand whether the difference in EV miR-21-5p associated with increased release of EVs under inflammatory conditions, NTA was performed to determine EV quantity and size distribution. No significant differences in either the size distribution or particle concentration were detected in MIN6 or EndoC cells, or in human islets after 24 hours of cytokine treatment (FIGS. 1g-1i). These data indicated that the cytokine-induced increase in beta cell EV miR-21-5p was specifically due to increases in vesicle cargo.

To understand if cytokine-induced increases in EV miR-21-5p were related to cytokine-induced beta cell apoptosis, EV-miR-21-5p was measured in MIN6 and EndoC cells treated with both cytokines and the pan-caspase inhibitor Z-VAD-FMK (FIGS. 1k and 1l). Cytokine-induced increases in EV miR-21-5p were partially abrogated by addition of Z-VAD-FMK. However, EV-miR-21-5p levels remained 2-fold increased compared to EVs from vehicle treated cells, indicating that cytokine-induced increases in beta cell EV miR-21-5p were only partially related to beta cell death.

EXAMPLE 2

Figures 2A, 2B, 2C, 2D, 2E, 2F, 2G, 2H:
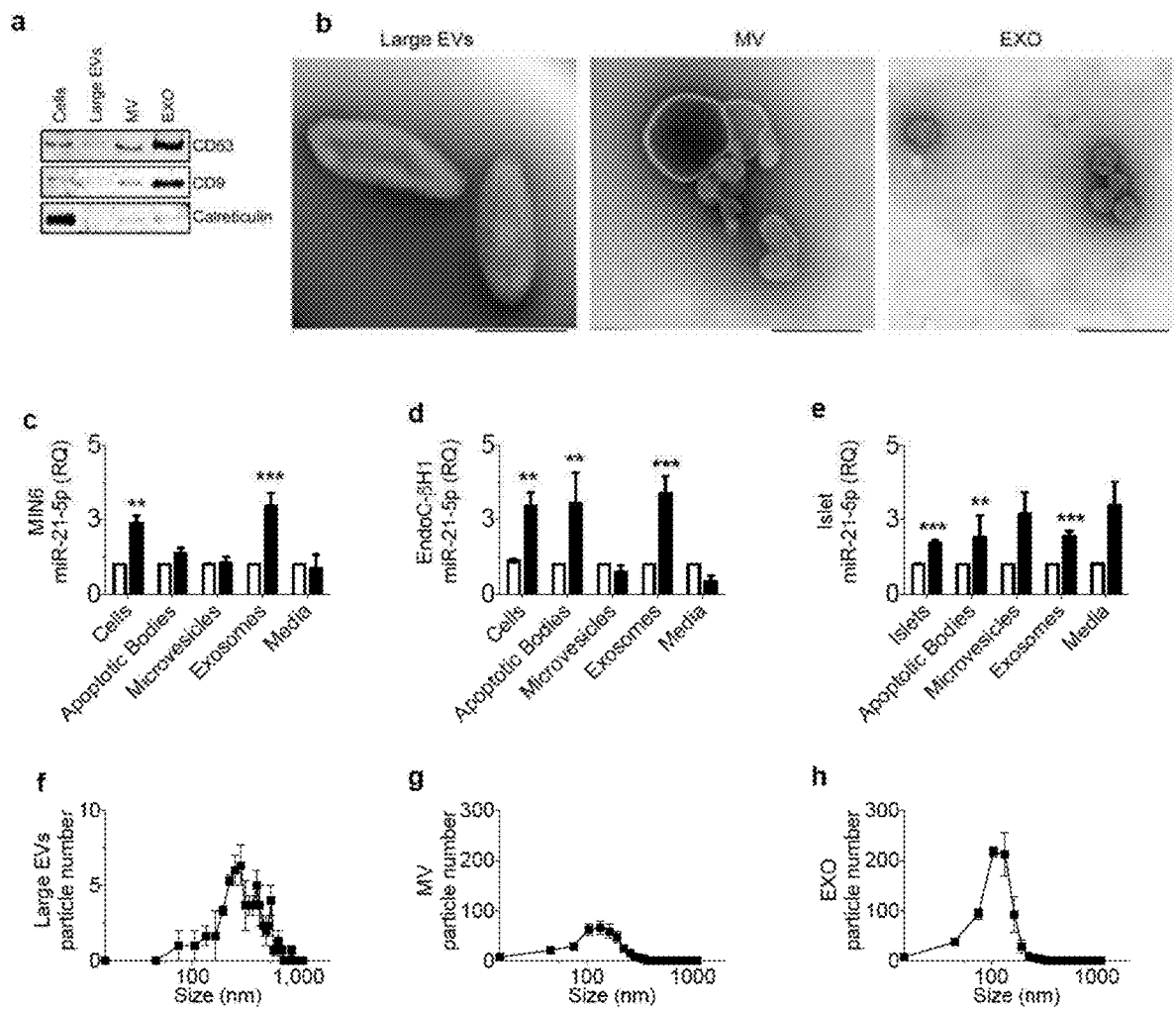
FIGS. 2a-2h depict cytokine-induced increases in beta cell EV miR-21-5p predominantly due to changes in exosome cargo. Media from vehicle (white bars) and cytokine-treated (black bars) MIN6 cells, EndoC cells, and human islets were separated by sequential centrifugation into large EV (apoptotic bodies), intermediate sized EV (microvesicles), and small EV (exosomes) fractions. EV-depleted media was also retained.

In this Example, whether cytokine-induced increase in beta cell EV miR-21-5p was due to a particular EV subtype was determined. Sequential ultracentrifugation was used to separate EVs by size, allowing for enrichment for larger vesicles (apoptotic bodies), intermediate sized vesicles (microvesicles), and smaller vesicles (exosomes). Immunoblot analysis and transmission electron microscopy (TEM) were performed to validate isolations (FIGS. 2a and 2b). Media remaining post-centrifugation was also collected to assess for presence and relative levels of EV-independent miR-21-5p release. miRNA quality and quantity were validated by spectral analysis, which revealed similar miRNA concentrations in EV preparations from the vehicle or cytokine treated samples. RT-qPCR of each fraction revealed that in MIN6 cells, miR-21-5p was only increased by cytokines in the exosome fraction (FIG. 2c). In EndoC cells and human islets, cytokine-induced increases in miR-21-5p were present in the apoptotic body and exosome fractions (FIGS. 2d and 2e). NTA of ultracentrifugation fractions revealed much higher total concentrations of exosomes compared to microvesicles or apoptotic bodies (FIGS. 2f-2h). In aggregate, these data indicated that exosomes were the predominant type of vesicle contributing to cytokine-induced increases in beta cell EV miR-21-5p.

EXAMPLE 3

Figures 3A, 3B, 3C, 3D, 3E, 3F, 3G, 3H:
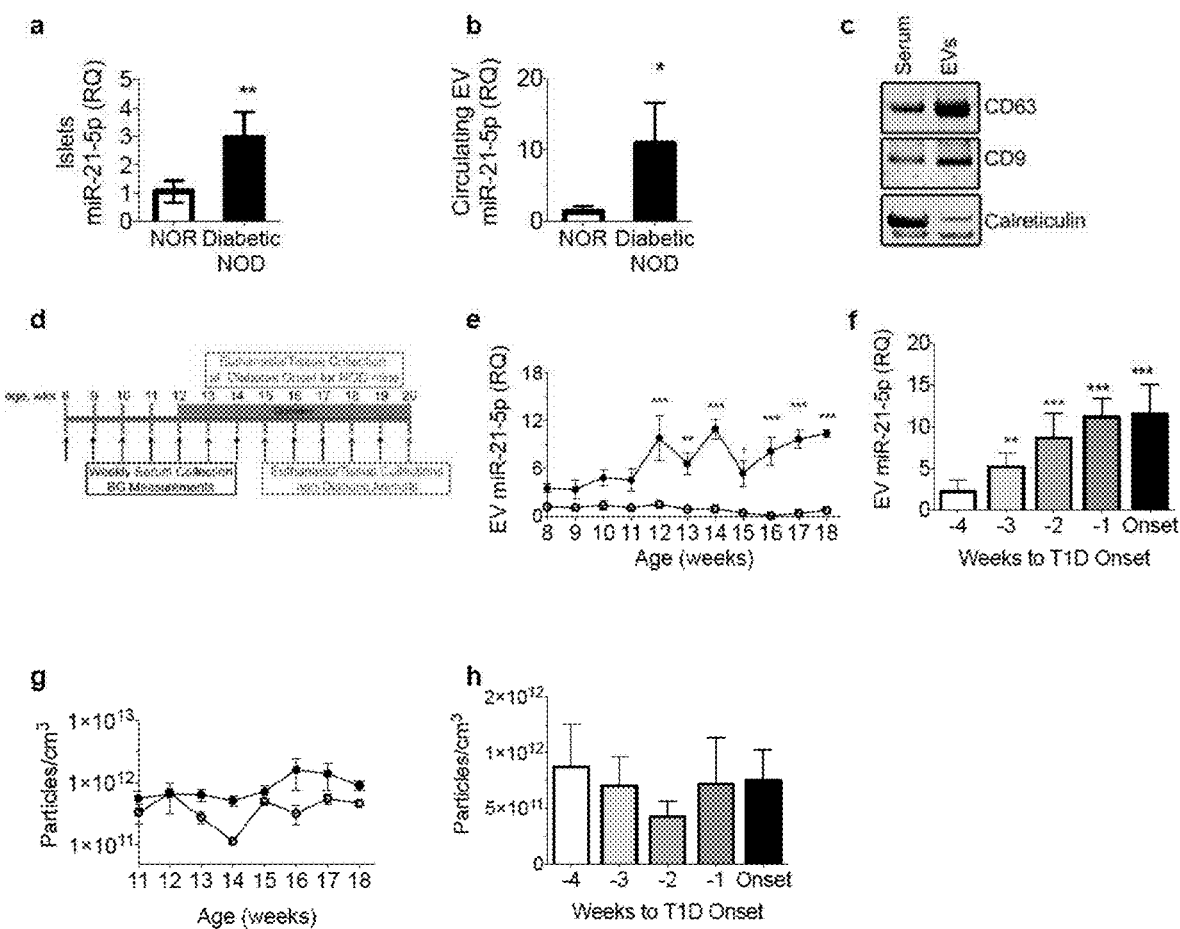
FIGS. 3a-3h depict elevated circulating EV miR-21-5p preceding onset of diabetes in NOD mice. RT-qPCR was performed to quantify relative levels of EV miR-21-5p in (FIG. 3a) islets and (FIG. 3b) terminal serum of diabetic NOD mice (n=4; black bars) compared to NOR controls (n=5; white bars).

In this Example, circulating EV was determined in NOD mice. Based on increased beta cell EV miR-21-5p release in response to cytokine exposure ex vivo, we predicted that circulating EV miR-21-5p would also be increased during in vivo development of type 1 diabetes. To determine whether circulating EV miR-21-5p was increased during in vivo development of type 1 diabetes, the NOD mouse model of type 1 diabetes was used. Consistent with the data in cytokine-treated cells and islets, islets from female diabetic NOD mice at the time of diabetes onset exhibited a 2.5-fold increase in miR-21-5p expression compared to islets from NOR controls (FIG. 3a). Next, EVs were isolated from terminal serum of diabetic mice. A ~10-fold increase in serum EV miR-21-5p was detected as compared to NOR control mice (FIG. 3b). EV isolation was validated by Western blotting for EV markers CD9 and CD63, which were enriched in the EV samples as compared to the original serum samples, whereas the ER marker calreticulin was grossly depleted in the EV isolates (FIG. 3c).

To determine changes in circulating EV miR-21-5p during type 1 diabetes development, weekly serial serum samples were collected from NOD mice starting at 8 weeks of age until the time of diabetes onset (FIG. 3d, n=7-9 per timepoint depending on time of diabetes onset). An age-dependent increase in miR-21-5p in the circulating EVs of prediabetic NOD mice starting at 12 weeks of age was observed (FIG. 3e). To determine temporal relationships to diabetes development, these values were normalized to age-matched NOR controls and the data was plotted based on relative time to diabetes onset, revealing a progressive increase in EV miR-21-5p starting 3 weeks before development of hyperglycemia (FIG. 3f). NTA of these circulating EVs revealed no significant changes in the EV concentration relative to age or relative to diabetes onset (FIGS. 3g-3h). These data confirm that progressive increases in serum EV miR-21-5p predated hyperglycemia during developing diabetes in this mouse model of type 1 diabetes mellitus.

EXAMPLE 4

In this Example, circulating EV miR-21-5p was determined in human children with new onset type 1 diabetes. Clinical serum samples from 19 pediatric volunteers with new onset type 1 diabetes and 16 healthy pediatric control participants were analyzed. Demographic characteristics are presented in Table 1.

TABLE 1

Demographic characteristics of human study participants.

| Variable | Healthy control (n = 16) | Type 1 diabetes (n = 19) | p value |
|---|---|---|---|
| Age (years) | 10.5 (9, 12) | 10.5 (8, 12) | 0.8579 |
| Male sex (%) | 62.5 | 62.5 | 1.00 |
| BMI percentile | 84 (72.5, 89.5) | 52.5 (32.5, 87.5) | 0.1343 |
| $HbA_{1C}$ (mmol/mol) (%) | n/a | 100 (89, 111) 11.3 (10.3, 12.3) | n/a |

Figures 4A, 4B, 4C, 4D, 4E, 4F, 4G, 4H, 4I, 4J, 4K:
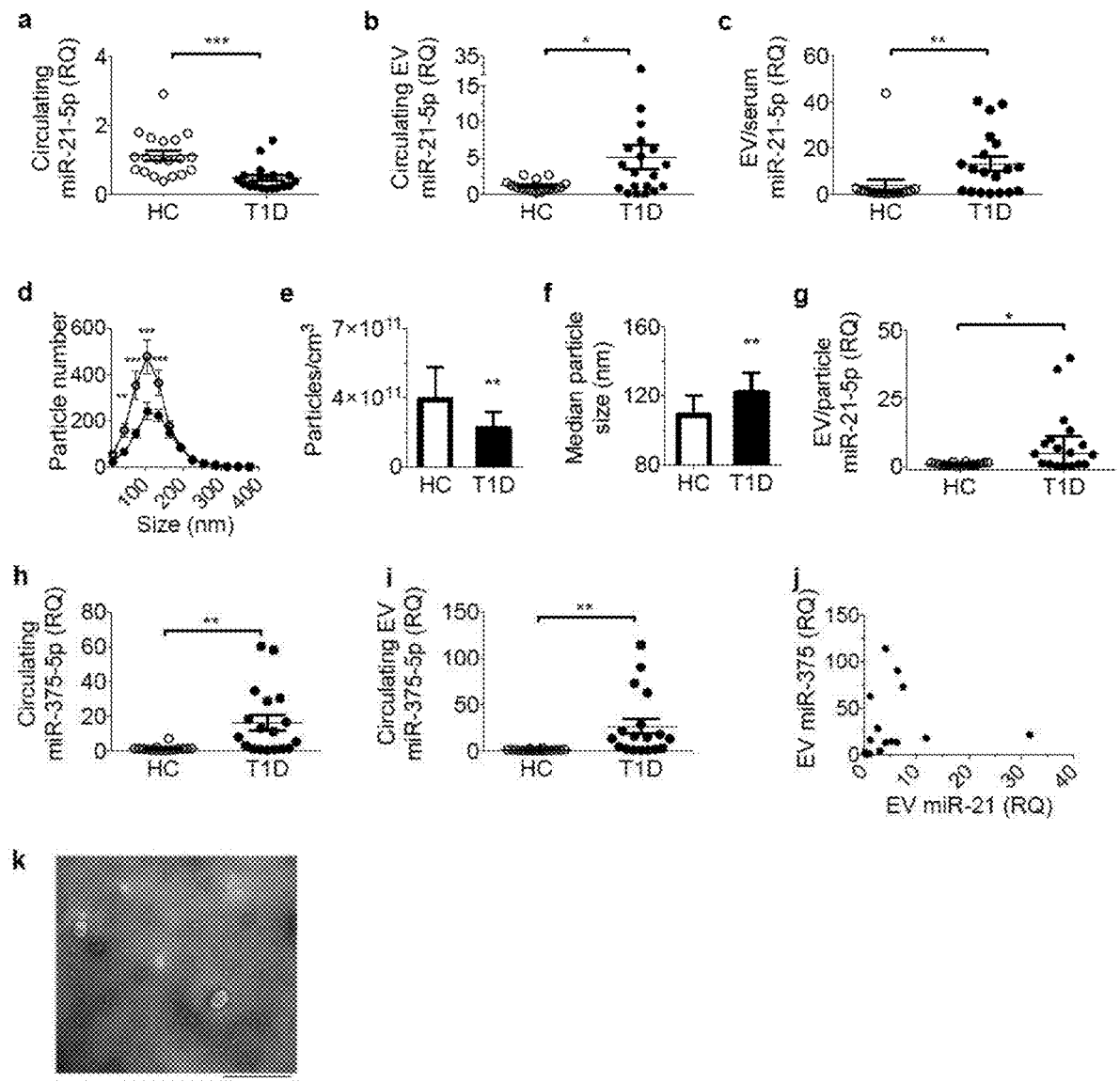
FIGS. 4a-4k depict elevated circulating EV miR-21-5p in children with new-onset type 1 diabetes. Serum samples from healthy pediatric controls (HC; white bars/circles) and children with new-onset type 1 diabetes (T1D; black bars/circles) were assessed for relative levels of circulating miR-21-5p in whole serum (FIG. 4a) and in circulating EVs (FIG. 4b; n=16-19/group).

Results are displayed as median (Interquartile range). BMI-body mass index, HbA1c—Hemoglobin A1c. No significant differences in age, sex, or BMI percentile for age were present between groups. Total serum miR-21-5p, total serum EVs and miR-21-5p were quantified from circulating EVs. In contrast to reports in longstanding type 1 diabetes, total serum miR-21-5p was decreased in participants with recent onset type 1 diabetes compared to controls (FIG. 4a). However, consistent with the in vitro and NOD mouse findings, levels of serum EV miR-21-5p were increased 5-fold in samples from participants with type 1 diabetes (FIG. 4b). Furthermore, when EV miR-21-5p levels were normalized to the total serum miR-21-5p, the miR-21-5p levels from circulating EVs of participants with type 1 diabetes were 12-fold higher than in controls, confirming that the increase in serum miR-21-5p was specific to EVs (FIG. 4c).

NTA on serum samples was used to assess differences in the overall concentration and size distribution of circulating EVs. This revealed reduced total circulating EVs in type 1 diabetes samples, specifically in smaller EVs (FIGS. 4d-4f). Normalization of serum EV miR-21-5p to total particle count also reflected increased serum EV miR-21-5p in individuals with type 1 diabetes, consistent with the in vitro findings that increased EV miR-21-5p was related to increased EV miR-21-5p cargo, rather than reflective of increased EV release (FIG. 4g). The relationship between serum EV miR-21-5p and age, BMI percentile, and $HbA_{1c}$ was determined for diabetic participants. In control individuals, younger age was related to higher EV miR-21-5p levels ($r_s$=−0.506, p=0.0474). However, this relationship was not present in participants with type 1 diabetes. No relationship between BMI percentile or $HbA_{1c}$ and EV miR-21-5p levels was detected. Similarly, no differences were detected based on sex.

Given that miR-21-3p originates from the same precursor miRNA as miR-21-5p, it was expected that circulating EV-miR-21-3p may also be increased in samples from participants with type 1 diabetes. To test this, miR-21-3p was measured in serum and serum EV samples. Consistent with prior reports in at-risk pre-diabetic individuals, total serum miR-21-3p was increased in samples from participants with type 1 diabetes. In contrast to serum EV miR- 21-5p, median serum EV miR-21-3p levels were lower in samples from the type 1 diabetes group, although individual values overlapped considerably with those of nondiabetic control participants. miR-375-5p, which has been proposed as a circulating biomarker of beta cell death, was also detected as a different miRNA of diabetes (FIGS. 4h and 4i). By contrast to miR-21-5p and miR-21-3p, in participants with type 1 diabetes, miR-375-5p was similarly increased in both serum and in serum EVs. Associations between the relative levels of serum EV miR-21-5p and miR-375-5p was determined among participants with diabetes (FIG. 4j). Although there was overlap in some individuals, the levels of the two microRNAs were not related overall, with examples of individuals with predominant elevations in either serum EV miR-21-5p or serum EV miR-375-5p. FIG. 4k is a representative image of a transmission electron micrograph of EV isolated from serum.

These Examples demonstrate that beta cell EV miR-21-5p cargo was increased in response to treatment with inflammatory cytokines. This increase was predominantly due to cytokine-induced effects on beta cell exosome miR-21-5p, and only partially blocked by inhibition of apoptosis. EV miR-21-5p can also serve as a biomarker of developing type 1 diabetes, in that progressive elevations in serum EV miR-21-5p preceded hyperglycemia in NOD mice, and were present in children with new onset type 1 diabetes. These Examples further demonstrate differences between circulating total miR-21-5p and EV miR-21-5p levels. The Examples demonstrating a decreased serum miR-21-5p among participants with type 1 diabetes are in contrast to several published reports of increased circulating miR-21-5p in individuals with more established type 1 diabetes

EXAMPLE 5

Figure 5:
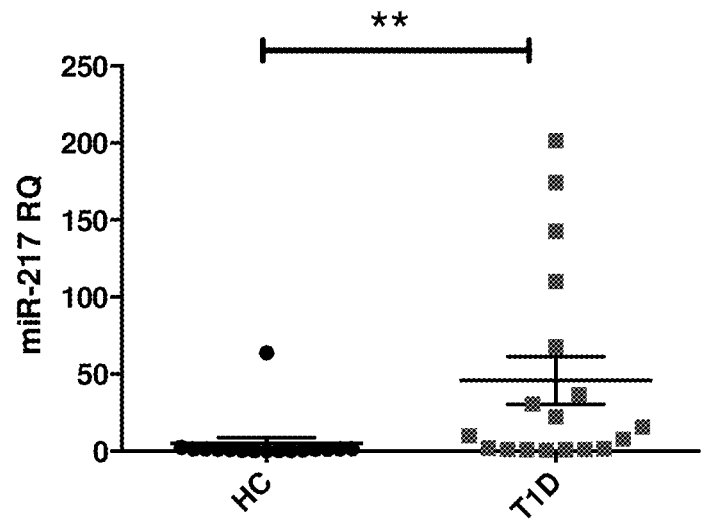
FIG. 5 depicts EV miR-217 in circulating EVs isolated from human serum of human control subjects (HC) and subjects with type 1 diabetes (T1D). Serum samples from healthy pediatric controls (HC; black circles) and children with new-onset type 1 diabetes (T1D; red squares circles) were assessed for relative levels of circulating miR-217 in circulating EVs. Total EVs were isolated from 50 uL of serum using an EXOQUICK precipitation kit. RNA was isolated and quantified in T1D samples relative to HC samples using q-RTPCR. n=16-19/group).

In this Example, circulating EV miR-217 was determined in human subjects with type 1 diabetes. Serum samples from healthy pediatric controls (HC) and children with new-onset type 1 diabetes (T1D) were assessed for relative levels of circulating miR-217 in circulating EVs. Total EVs were isolated from 50 µL of serum using an EXOQUICK precipitation kit. RNA was isolated and quantified in T1D samples relative to HC samples using q-RTPCR (n=16-19/group). FIG. 5 demonstrates that miR-217 was increased in subjects with type 1 diabetes.

EXAMPLE 6

Figure 6:
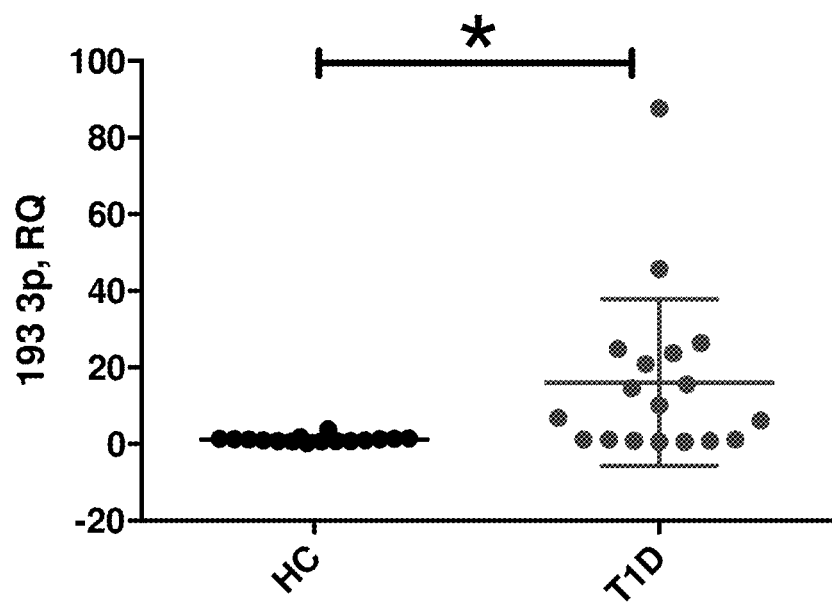
FIG. 6 depicts EV miR-193-3p in circulating EVs isolated from human serum of human control subjects (HC) and subjects with type 1 diabetes (T1D). Serum samples from healthy pediatric controls (HC; black circles) and children with new-onset type 1 diabetes (T1D; red squares circles) were assessed for relative levels of circulating miR-21-5p in circulating EVs. Total EVs were isolated from 50 uL of serum using an EXOQUICK precipitation kit. RNA was isolated and quantified in T1D samples relative to HC samples using q-RTPCR. n=16-19/group).

In this Example, circulating EV miR-193-3p was determined in human subjects with type 1 diabetes. Serum samples from healthy pediatric controls (HC; black circles) and children with new-onset type 1 diabetes (T1D; red squares circles) were assessed for relative levels of circulating miR-21-5p in circulating EVs. Total EVs were isolated from 50 µL of serum using an Exoquick precipitation kit. RNA was isolated and quantified in T1D samples relative to HC samples using q-RTPCR. n=16-19/group). FIG. 6 demonstrates that miR-193-3p was increased in subjects with type 1 diabetes.

EXAMPLE 7

Figure 7:
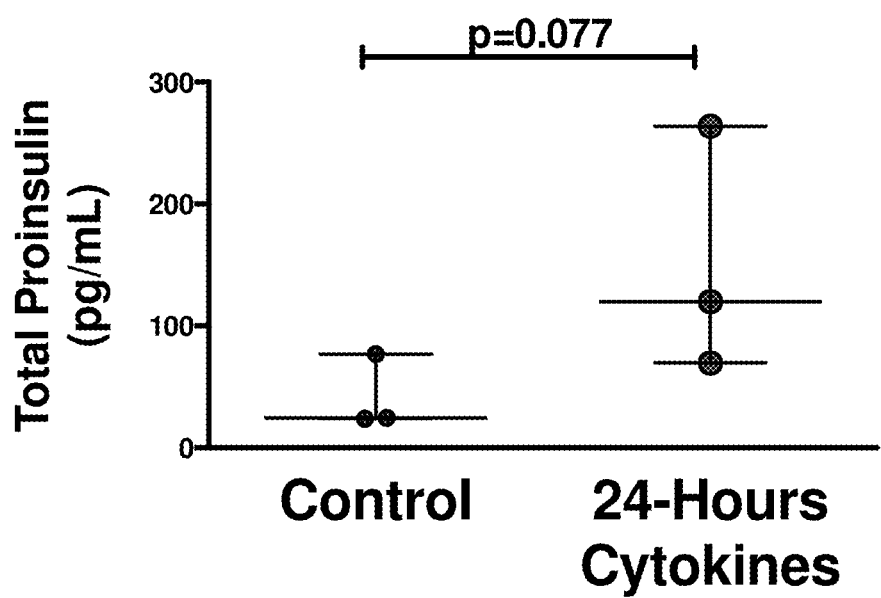
FIG. 7 depicts proinsulin protein in EVs from cytokine treated beta cells and control beta cells. EndoC BH1 human clonal beta cells were treated with a cytokine mix of TNF-α, IFN-γ, and IL1-β, or vehicle control for 24 hours. Exosomes were isolated from cell supernatant using sequential ultracentrifugation and proinsulin was measured in protein lysates using a human total proinsulin ELISA.
Figure 8A:
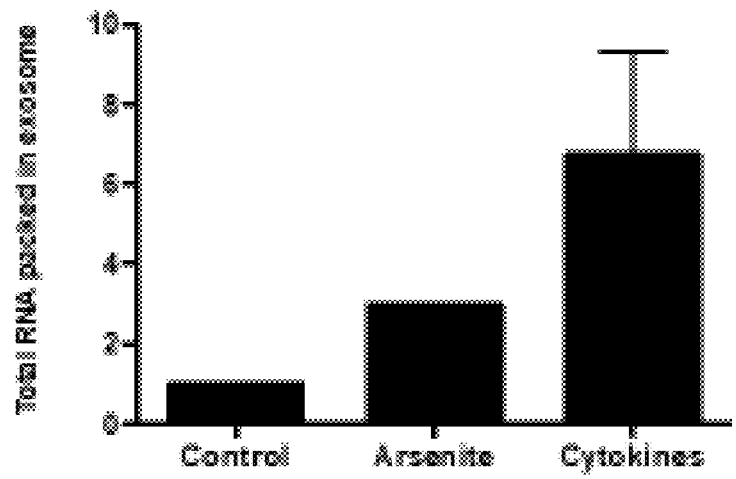
Figure 8B:
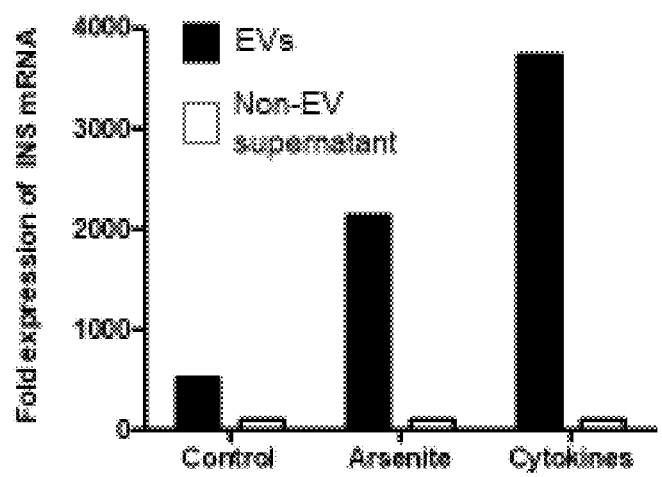
Figure 9A:
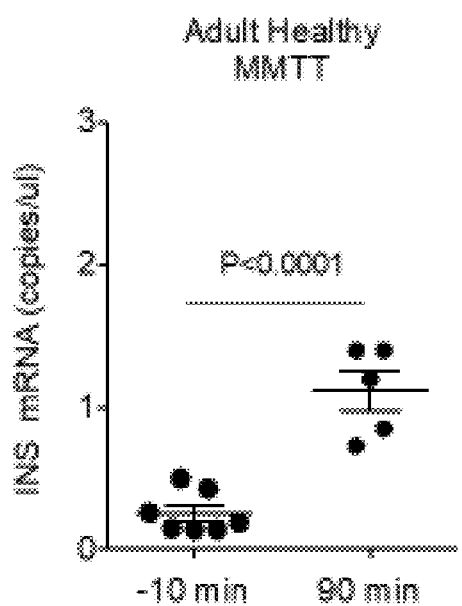
FIGS. 9A and 9B provides graphs demonstrating the levels of circulating insulin mRNA following MMTT in adult healthy mice (FIG. 9A) and in TrialNet PTP mice.
Figure 9B:
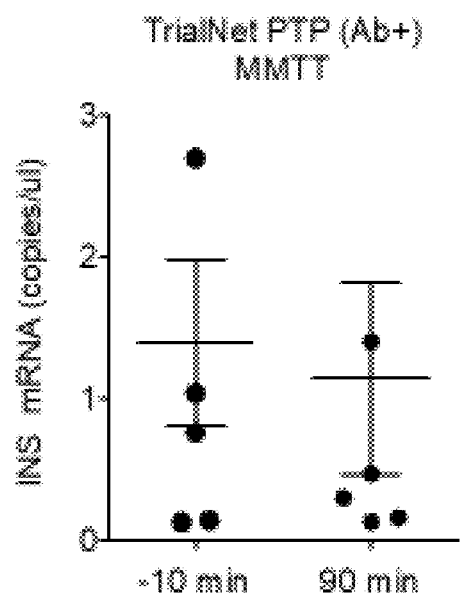
Figure 10:
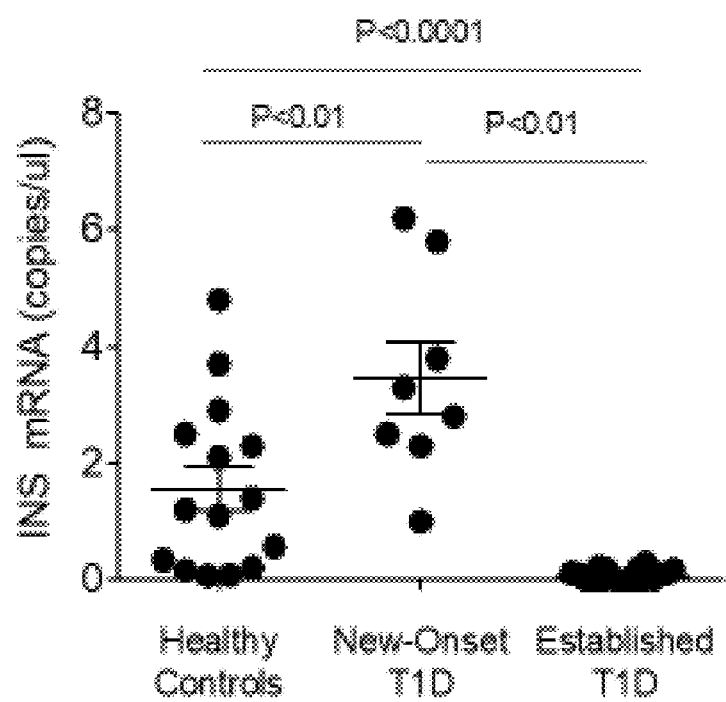
FIG. 10 is a graph demonstrating increases in circulating INS mRNA in new-onset type 1 diabetes (T1D) vs established T1D.
Figure 11A:
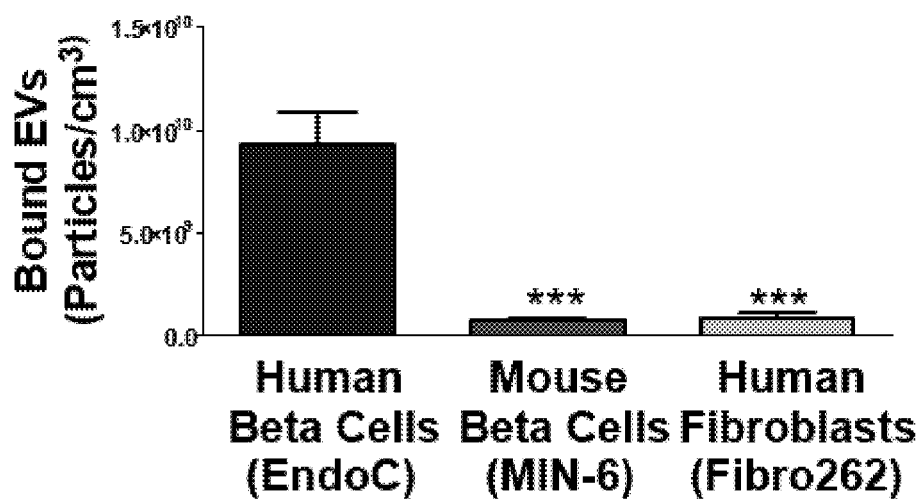
FIGS. 11A and 11B.
Figure 11B:
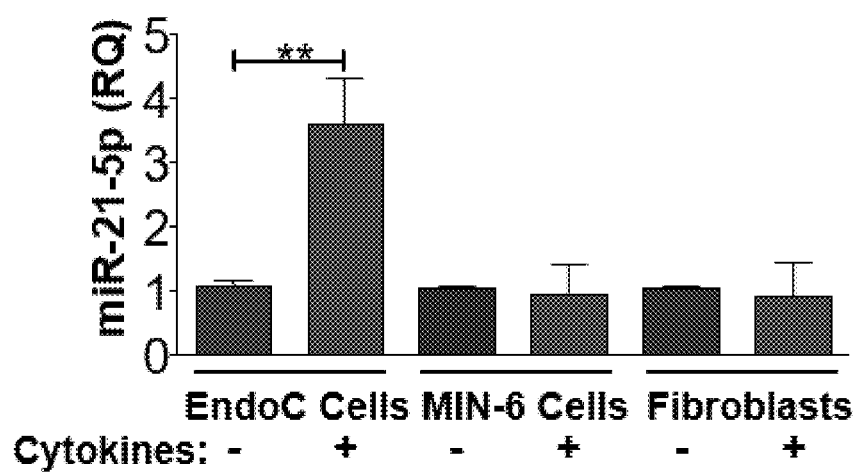

In this Example, EV proinsulin was determined in beta cells treated with cytokines. EndoC BH1 human clonal beta cells were treated with a cytokine mix of TNF-α, IFN-γ, and IL1-β, or vehicle control for 24 hours. Exosomes were isolated from cell supernatant using sequential ultracentrifugation and proinsulin was measured in protein lysates using a human total proinsulin ELISA. FIG. 7 demonstrates that proinsulin was increased in EVs of cytokine treated beta cells.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

The invention claimed is:

1. A method of treating a patient susceptible to hyperglycemia, said method comprising
identifying the patient as susceptible to hyperglycemia, wherein said identification step comprises
obtaining the patient's biological sample;
isolating beta cell extracellular vesicles from said sample through the use of an extracellular vesicle marker selected from the group consisting of CD9 and CD63; and
quantitating two or more miRNAs selected from the group consisting of miR-21-5p, miR-21-3p, miR-217 and miR-193-3p associated with said isolated extracellular vesicles, wherein elevated levels of two or more of said miRNAs associated with said isolated extracellular vesicles identifies a patient as being susceptible to hyperglycemia; and treating said identified patient susceptible to hyperglycemia using standard anti-diabetes therapies.

2. The method of claim 1 wherein said elevated levels of said two or more miRNAs associated with said isolated extracellular vesicles are determined based on a comparison of the identified patient's levels of said two or more miRNAs associated with said isolated extracellular vesicles to levels of said two or more miRNAs associated with isolated extracellular vesicles in a control patient.

3. The method of claim 1 wherein said elevated levels of said two or more miRNAs associated with said isolated extracellular vesicles are determined based on a comparison of the identified patient's levels of said two or more miRNAs associated with said isolated extracellular vesicles in a first sample relative to levels of said two or more miRNAs associated with said isolated extracellular vesicles in a second sample recovered from the same patient, wherein there is a temporal spacing between the recovery of said first and second sample, and said second sample has an increase in the levels of said two or more miRNAs associated with said isolated extracellular vesicles relative to the first sample.

4. The method of claim 3 wherein the temporal spacing is selected from 1 day, 1 week, 1 month, 1 year or 2 years.

5. The method of claim 1 wherein the step of identifying the patient as susceptible to hyperglycemia comprises detecting miR-21-5p, miR-21-3p, miR-217 and miR-193-3p associated with circulating extracellular vesicles in a patient, wherein said detecting step comprises providing a plasma or serum sample obtained from said patient;

isolating beta cell extracellular vesicles from said sample through the use of an extracellular vesicle marker selected from the group consisting of CD9 and CD63; and quantitating the miR-21-5p, miR-21-3p, miR-217 and miR-193-3p associated with said isolated extracellular vesicles, wherein the detection of elevated levels of two or more of miR-21-5p, miR-21-3p, miR-217 and miR-193-3p associated with said isolated extracellular vesicles identifies a patient as being susceptible to hyperglycemia.

6. The method of claim 5 wherein the detection of elevated levels of three or more of miR-21-5p, miR-21-3p, miR-217 and miR-193-3p associated with said isolated extracellular vesicles identifies a patient as being susceptible to hyperglycemia.

7. The method of claim 5 wherein the patient sample is a serum sample, and the isolation step comprises immunoprecipitation of the extracellular vesicles based on the presence of the extracellular vesicle marker CD9.

8. A method of treating a patient susceptible to hyperglycemia, said method comprising identifying the patient as susceptible to hyperglycemia, wherein said identification step comprises obtaining the patient's biological sample;

isolating beta cell extracellular vesicles from said sample through the use of an extracellular vesicle marker selected from the group consisting of CD9 and CD63; and quantitating two or more miRNAs selected from the group consisting of miR-21-5p, miR-21-3p, miR-217 and miR-193-3p associated with said isolated extracellular vesicles, wherein detection of elevated levels of two or more of said miRNAs associated with said isolated extracellular vesicles identifies the patient as being susceptible to hyperglycemia; and treating said identified patient susceptible to hyperglycemia by administering insulin to said identified patients.

* * * * *